(12) United States Patent
Rousselle

(10) Patent No.: US 9,260,507 B2
(45) Date of Patent: Feb. 16, 2016

(54) PEPTIDE PROMOTING CELL ADHESION AND MIGRATION

(75) Inventor: Patricia Rousselle, Lyons (FR)

(73) Assignees: Symatese, Chaponost (FR); Centre National De La Recherche Scientifique, Pau (FR); Universite Claude Bernard Lyon I, Villeurbanne (FR)

(*) Notice: Subject to any disclaimer, the term of this patent is extended or adjusted under 35 U.S.C. 154(b) by 394 days.

(21) Appl. No.: 13/255,299

(22) PCT Filed: Mar. 15, 2010

(86) PCT No.: PCT/FR2010/050458
§ 371 (c)(1),
(2), (4) Date: Sep. 8, 2011

(87) PCT Pub. No.: WO2010/103254
PCT Pub. Date: Sep. 16, 2010

(65) Prior Publication Data
US 2012/0114617 A1 May 10, 2012

(30) Foreign Application Priority Data
Mar. 13, 2009 (FR) ...................................... 09 01168

(51) Int. Cl.
| A61K 8/64 | (2006.01) |
| C07K 7/06 | (2006.01) |
| C12N 5/071 | (2010.01) |
| A61K 38/08 | (2006.01) |
| A61Q 19/00 | (2006.01) |
| C07K 14/78 | (2006.01) |
| A61K 38/00 | (2006.01) |

(52) U.S. Cl.
CPC *C07K 14/78* (2013.01); *A61K 38/00* (2013.01)

(58) Field of Classification Search
CPC ................................ A61K 38/00; C07K 14/78
See application file for complete search history.

(56) References Cited

U.S. PATENT DOCUMENTS

| 5,594,113 A * | 1/1997 | Wainwright et al. ......... 530/395 |
| 7,208,475 B2 * | 4/2007 | Castillo .................. C07K 14/78 424/184.1 |
| 7,314,724 B2 | 1/2008 | Castillo et al. |

FOREIGN PATENT DOCUMENTS

| CN | 101058601 A * 10/2007 ............. A61K 38/00 |
| JP | 2006063033 A 3/2006 |
| WO | WO-00/66731 A2 11/2000 |
| WO | WO-2006/018551 A1 2/2006 |
| WO | WO-2006/025646 A1 3/2006 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
SR Herzog, Wound Coverage with cultured autologous keratinocytes: use after burn wound excision, including biopsy followup, J Trauma, Feb. 1998;28(2):195-198, abstract provided only.*
International Search Report for PCT/FR2010/050458 mailed Aug. 3, 2010 (4 pgs.).
Vives, Romain R. et al., "A Novel Strategy for Defining Critical Amino Acid Residues Involved in Protein/Glycosaminoglycan Interactions", Dec. 24, 2004 The Journal of Biomedical Chemistry, vol. 279, No. 22 (pp. 54327-54333).
Bachy, Sophie, et al., "Syndecan-1 Interaction With the LG4/5 Domain in Laminin-332 is Essential for Keratinocyte Migration, 2008 Journal of Cellular Physiology", 214 (pp. 238-249).
Okamoto, Osamu et al., "Normal Human Keratinocytes Bind to the a3LG4/5 Domain of Unprocessed Laminin-5 through the Receptor Syndecan-1", Jouornal of Biological Chemistry, Nov. 7, 2003, vol. 278, No. 45 (pp. 44168-44177).
Hashimoto, Tadashi et al., "Development of alginate wound dressings linked with hybrid peptides derived from laminin and elastin", 2004 Biomaterials 25 (pp. 1407-1414).
Suzuki, Nobuharu et al., "Functional Sites in the Laminin Alpha Chains", 2005 Connective Tissue Research, 46 (pp. 142-152).
Amano, Satoshi et al., "Bone Morphogenetic Protein 1 Is an Extracellular Processing Enzyme of the Laminin 5 γ2 Chain", 2000 Journal of Biological Chemistry, vol. 275, No. 30 (pp. 22728-22735).
Aumailley, Monique et al., "Laminins of the dermo—epidermal junction", 1999 Matrix Biology 18 (pp. 19-28).
Baker, Scott E. et al., "Laminin-5 and hemidesmosomes: role of the α3 chain subunit in hemidesmosome stability and assembly", 1996 Journal of Cell Science 109 (pp. 2509-2520).
Belin, Virginie et al., "Production of a recombinantly expressed laminin fragment by HEK293-EBNA cells cultured in suspension in a dialysis-based bioreactor", 2006 Protein Expression and Purification 48 (pp. 43-48).

(Continued)

*Primary Examiner* — Julie Ha
*Assistant Examiner* — Erinne Dabkowski
(74) *Attorney, Agent, or Firm* — Harris Beach PLLC

(57) ABSTRACT

A peptide is provided with a defined sequence present in the alpha3 chain of the LG4 globule of laminin 332 (laminin 5), and peptides with sequences homologous to the peptide with the defined sequence capable of binding to the syndecan-1 receptor. Pharmaceutical or cosmetic compositions containing the peptide are provided. The peptide is used in the area of tissue healing and regeneration or as an adjuvant in culture media intended for epidermal or epithelial reconstruction. The synthetic peptide comprises the sequence KKLRIK-SKEK (SEQ ID NO: 1) or a sequence of identical size, in which the K residue (in position 1) and the R residue (in position 4) are conserved, the sequence being able to bind to the syndecan-1 receptor.

25 Claims, 15 Drawing Sheets

(56) References Cited

OTHER PUBLICATIONS

Figure 1:
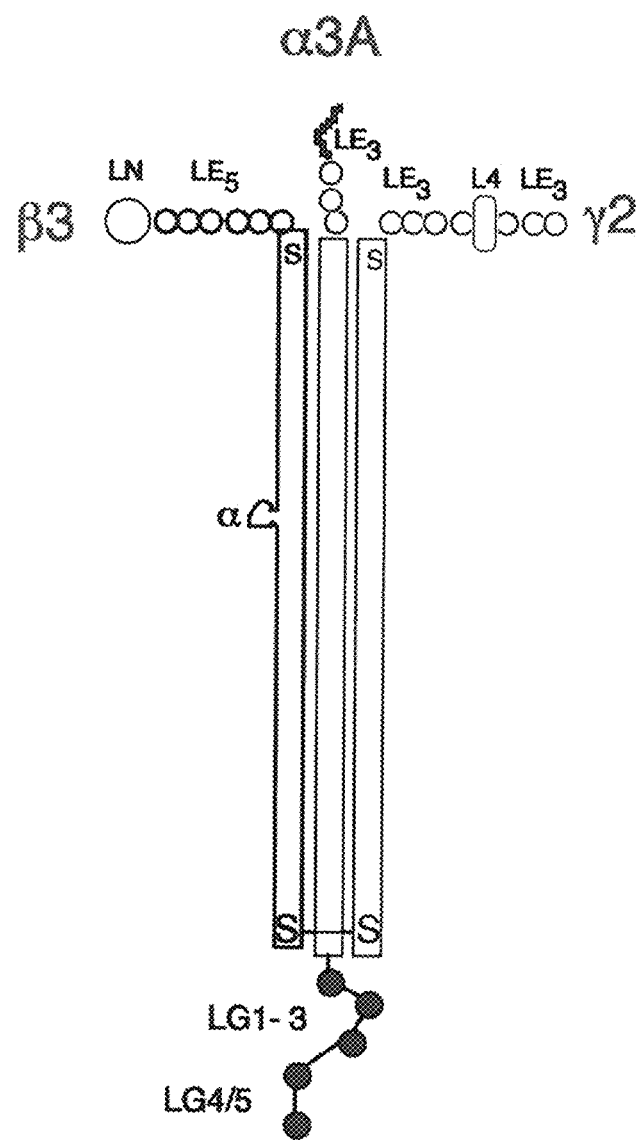

Bernfield, M. et al., "Functions of cell surface heparan sulfate proteglycans", 1999 Annual Review Biochemistry 68 Abstract (1 pg.).
Decline, Francoise et al., Keratinocyte Motility Induced by TGF-$\beta$1 Is Accompanied by Dramatic Changes in Cellular Interactions With Laminin 5, 2003 Cell Motility and the Cytoskeleton 54 (pp. 64-80).
Decline, Francoise et al., "Keratinocyte migration requires $\alpha 2\beta 1$ integrin-mediated interaction with the laminin 5 $\gamma 2$ chain", 2000 Journal of Cell science 114 (pp. 811-823).
Elenius, Klaus et al., "Induced Expression of Syndecan in Healing Wounds", Aug. 1991 Journal of Cell Biology, vol. 114, No. 3 (pp. 585-595).
Frank, Diane E. et al., "Laminin 5 deposition regulates keratinocyte polarization and persistent migration", 2004 Journal of Cell Science 117 (8), (pp. 1351-1363).
Ghohestani, Reza F. et al., Molecular Organization of the Cutaneous Basement Membrane Zone, 2001 Clinics in Dermatology 19 (pp. 551-562).
Goldfinger, Lawrence E. et al., "Processing of Laminin-5 and Its Functional Consequences: Role of Plasmin and Tissue-type Plasminogen Activator", Apr. 6, 1998 Journal of Cell Biology, vol. 141, No. 1 (pp. 255-265).
Goldfinger, Lawrence E. et al., "The $\alpha 3$ laminin subunit, $\alpha 6\beta 4$ and $\alpha 3\beta 1$ integrin coordinately regulate wound healing in cultured epithelial cells and in the skin", 1999 Journal of Cell Science 112 (pp. 2615,2629).
Hynes, Richard O., "Integrins: Versatility, Modulation, and Signaling in Cell Adhesion", Apr. 3, 1992, Cell, vol. 69 (pp. 11-25).
Jaakkola, Panu et al., "Wound reepithelialization activates a growth factor-responsive enhancer in migrating keratinocytes", Aug. 1998 FASEB Journal, vol. 12 (pp. 959-969).
Lampe, Paul D. et al., "Cellular Interaction of Integrin $\alpha 3\beta 1$ with Laminin 5 Promotes Gap Junctional Communication", Dec. 14, 1998 Jouornal of Cell Biology, vol. 143, No. 6 (pp. 1735-1747).
Larjava, Hannu et al., "Expression of Integrins and Basement Membrane Components by Wound Keratinocytes", Sep. 1993, J. Clin. Invest. vol. 92 (pp. 1425-1435).
Marinkovich, M. Peter et al., "The Anchoring Filament Protein Kalinin Is Synthesized and Secreted as a High Moleuclar Weight Precursor", Sep. 5, 1992 Journal of Biological Chemistry, vol. 267, No. 25 (pp. 17900-17906).
Masuda, Ryuji, et al., "A novel cell-adhesive scaffold material for delivering keratinocytes reduces granulation tissue in dermal wounds", 2009 Wound Repair and Regeneration 17 (pp. 127-135).
Nguyen, Beth P. et al., "Deposition of laminin 5 in epidermal wounds regulates integrin signaling and adhesion", 2000 Current Opinion in Cell Biology 12 (pp. 554-562).
Niessen, C.M. et al., "The $\alpha 6\beta 4$ Integrin Is a Receptor for both Laminin and Kalinin", 1994 Experimental Cell Research 211 (pp. 360-367).
Oksala O. et al., "Expression of Heparan Sulphate and Small Dermatan/Chondroitin Sulphate Proteoglycans in Chronically Inflamed Human Periodontium", 1997 Journal of Dental Research, vol. 76 No. 6 (pp. 1250-1259).
Rousselle, Patricia et al., "Kalinin: An Epithelium-Specific Basement Membrane Adhesion Molecule That Is a Component of Anchoring Filaments", Aug. 1991 Journal of Cell Biology, vol. 114, No. 3 (pp. 567-576).
Rousselle, Patricia et al., "Laminin 5 Binds the NC-1 Domain of Type VII Collagen", Aug. 11, 1997 Journal of Cell Biology, vol. 138, No. 3 (pp. 719-728).
Rousselle, Patricia et al., "Kalinin Is More Efficient than Laminin in Promoting Adhesion of Primary Keratinocytes and Some Other Epithelial Cells and Has a Different Requirement for Integrin Receptors", Apr. 1994 Journal of Cell Biology, vol. 125, No. 1 (pp. 205-214).
Ryan, Maureen C. et al., "Cloning of the LamA3 Gene Encoding the $\alpha 3$ Chain of the Adhesive Ligand Epiligrin", Expression in Wound Repair, Sep. 9, 1994 Journal of Biological Chemistry, vol. 269, No. 36 (pp. 22779-22787).
Ryan, Maureen C. et al., "Targeted Disruption of the *LAMA3* Gene in Mice Reveals Abnormalities in Survival and Late Stage Differentiation of Epithelial Cells", Jun. 14, 1999, Journal of Cell Biology, vol. 145, No. 6 (pp. 1309-1323).
Sigle, Randy O. et al.,"Globular domains 4/5 of the laminin $\alpha 3$ chain mediate deposition of precursor laminin 5", 2004 Journal of Cell Science 117 (pp. 4481-4494).
Sonnenberg, A. et al., "Formation of hemidesmosomes in cells of a transformed murine mammary tumor cell line and mechanisms involved in adherence of these cells to laminin and kalinin", 1992 Journal of Cell Science 106 (pp. 1083-1102).
Stepp, Mary Ann et al., "Defects in keratinocyte activation during wound healing in the syndecan-1-deficient mouse", 2002 Journal of Cell Science 115 (pp. 4517-4531).
Sulka, Beatrice et al., "Tyrosine Dephosphorylation of the Syndecan-1 PDZ Binding Domain Regulates Syntenin-1 Recruitment", Apr. 17, 2009 Journal of Biological Chemistry, vol. 284, No. 16 (pp. 10659-10671).
Timpl, Rupert et al., "Structure and function of laminin LG modules", 2000 Matrix Biology 19 (pp. 309-317).
Tisi, Dominic et al., "Structure of the C-terminal laminin G-llike domain pair of the laminin $\alpha 2$ chain harbouring binding sites for $\alpha$-dystroglycan and heparin", 2000 EMBO Journal, vol. 19, No. 7 (pp. 1432-1440).
Tunggal, Lucy et al., "Defective Laminin 5 Processing in Cylindroma Cells", Feb. 2002 American Journal of Pathology, vol. 160, No. 2 (pp. 459-468).
Utani, Atsushi et al., "A Unique Sequence of the Lamimin $\alpha 3$ G Domain Binds to Heparin and Promotes Cell Adhesion through Syndecan-2 and -4", Aug. 3, 2001 Journal of Biological Chemistry, vol. 276, No. 31 (pp. 28779-28788).
Woods, Anne et al., "Integrin Modulation by Lateral Association", Aug. 11, 2000 Journal of Biological Chemistry, vol. 275, No. 32 (pp. 24233-24236).
Araki, Eri et al., "Clustering of Syndecan-4 and Integrin $\beta 1$ by Laminin $\alpha 3$ Chain-derived Peptide Promotes Keratinocyte Migration," Jul. 1, 2009, Molecular Biology of the Cell, vol. 20 (pp. 3012-3024).
Kreuger Johan et al., "Interactions between heparan sulfate and proteins: the concept of specificity," Jul. 31, 2006, Journal of Cell Biology, vol. 174, No. 3 (pp. 323-327).

* cited by examiner

```
                    DTP VASPRSVKVW ODACSPLPKT 1360
QANHGALQFG DIPTSHLLFK LPQELLKPRS QFAVDMQTTS 1400
SRGLVPHTGT KNSFMALYLS KGRLVFALGT DGKKLRIKSK 1440
EKCNDGKWHT VVFGHDGEKG RLVVDGLRAR EGSLPGNSTI 1480
SIRAPVYLGS PPSGKPKSLP TNSFVGCLKN FQLDSKPLYT 1520
PSSSFGVSSC LGGPLEKGIY FSEEGGHVVL AHSVLLGPEF 1560
KLVFSIRPRS LTGILIHIGS QPGKHLCVYL EAGKVTASMD 1600
SGAGGTSTSV TPKQSLCDGQ WHSVAVTIKQ HILHLELDTD 1640
SSYTAGQIPF PPASTQEPLH LGGAPANLTT LRIPVWKSFF 1680
GCLRNIHVNH IPVPVTEALE VQGPVSLNGC PDQ        1713
```

(SEQ ID NO: 39)

Figure 2

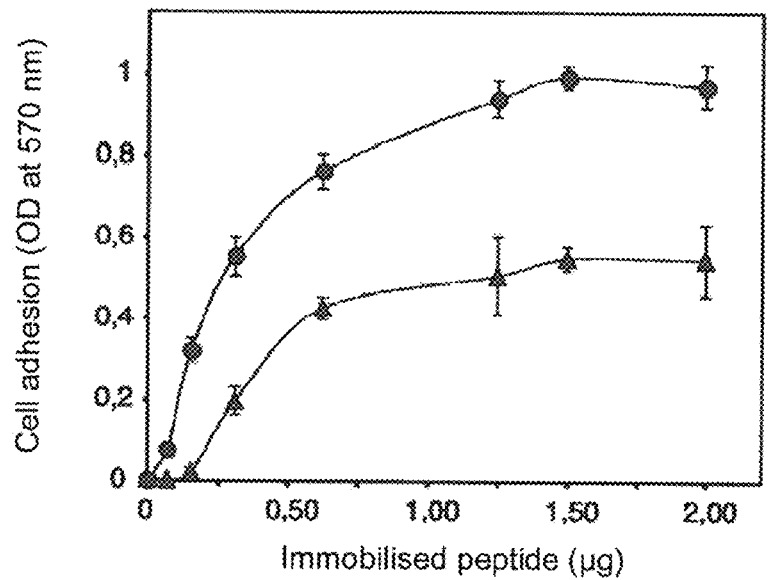
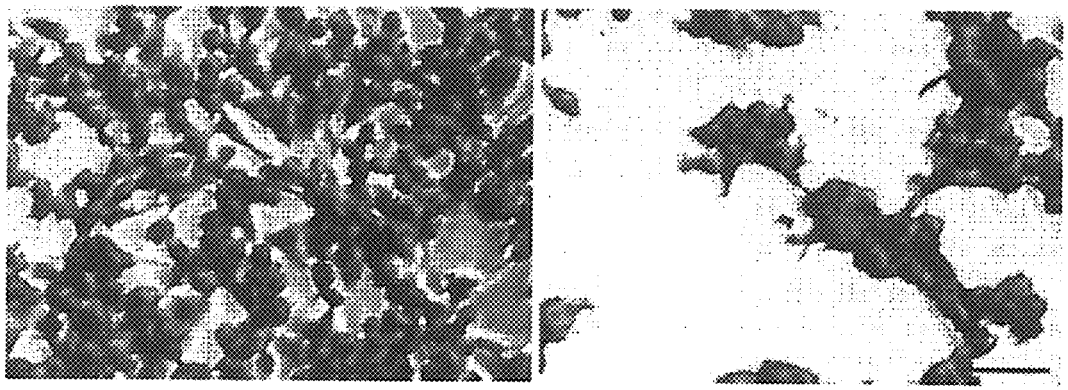
Figure 6

| | | |
|---|---|---|
| T+ | KKLRIKSKEK | (SEQ ID NO: 1) |
| A1 | AKLRIKSKEK | (SEQ ID NO: 22) |
| A2 | KALRIKSKEK | (SEQ ID NO: 2) |
| A3 | KKARIKSKEK | (SEQ ID NO: 3) |
| A4 | KKLAIKSKEK | (SEQ ID NO: 23) |
| A5 | KKLRAKSKEK | (SEQ ID NO: 4) |
| A6 | KKLRIASKEK | (SEQ ID NO: 5) |
| A7 | KKLRIKAKEK | (SEQ ID NO: 24) |
| A8 | KKLRIKSAEK | (SEQ ID NO: 6) |
| A9 | KKLRIKSKAK | (SEQ ID NO: 7) |
| A10 | KKLRIKSKEA | (SEQ ID NO: 8) |

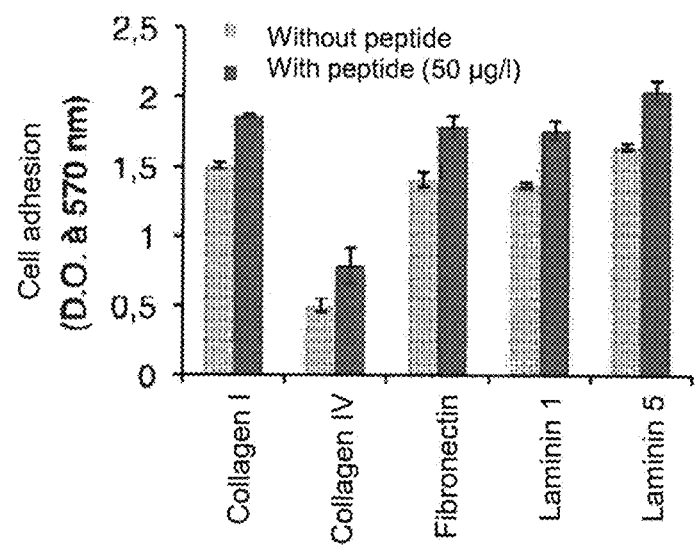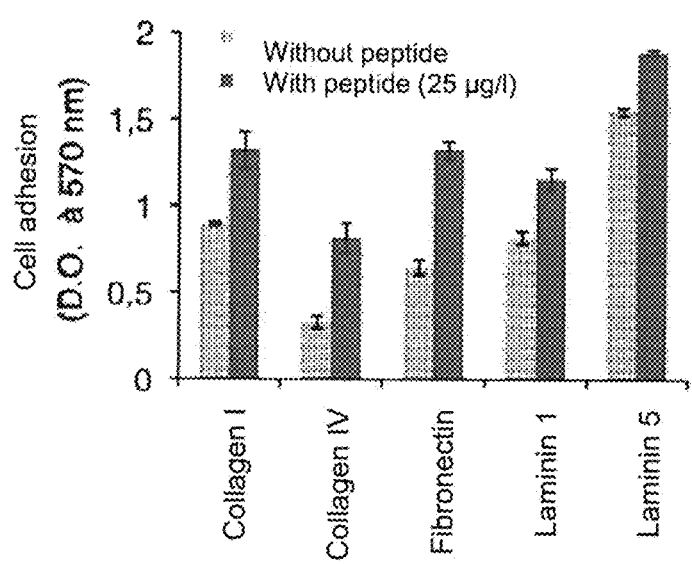
Figure 13

SEQUENCE LISTING

```
<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Synthesized sequence

<400> SEQUENCE: 1

Lys Lys Leu Arg Ile Lys Ser Lys Glu Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthesized sequence

<400> SEQUENCE: 2

Lys Ala Leu Arg Ile Lys Ser Lys Glu Lys
1               5                   10

<210> SEQ ID NO 3
<211> LENGTH: 10
<212> TYPE: PRT
<213> ORGANISM: Artificial Sequence
```

```
<220> FEATURE:
<223> OTHER INFORMATION: Synthesized sequence

<400> SEQUENCE: 3

Lys Lys Ala Arg Ile Lys Ser Lys Glu Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthesized sequence

<400> SEQUENCE: 4

Lys Lys Leu Arg Ala Lys Ser Lys Glu Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthesized sequence

<400> SEQUENCE: 5

Lys Lys Leu Arg Ile Ala Ser Lys Glu Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthesized sequence

<400> SEQUENCE: 6

Lys Lys Leu Arg Ile Lys Ser Ala Glu Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthesized sequence

<400> SEQUENCE: 7

Lys Lys Leu Arg Ile Lys Ser Lys Ala Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthesized sequence

<400> SEQUENCE: 8

Lys Lys Leu Arg Ile Lys Ser Lys Glu Ala
1               5                   10

<210> SEQ ID NO 9
<211> LENGTH: 10
<212> TYPE: PRT
<213> ORGANISM: Artificial Sequence
```

```
<220> FEATURE:
<223> OTHER INFORMATION: Synthesized sequence

<400> SEQUENCE: 9

Lys Lys Leu Arg Leu Arg Ser Lys Glu Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthesized sequence

<400> SEQUENCE: 10

Lys Lys Leu Arg His Lys Ser Lys Glu Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthesized sequence

<400> SEQUENCE: 11

Lys Lys Leu Arg Thr Lys Ser Lys Glu Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthesized sequence

<400> SEQUENCE: 12

Lys Lys Leu Arg Lys Lys Ser Lys Glu Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthesized sequence

<400> SEQUENCE: 13

Lys Lys Leu Arg Ser Lys Ser Lys Glu Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthesized sequence

<400> SEQUENCE: 14

Lys Lys Leu Arg Ile Lys Leu Lys Glu Lys
1               5                   10

<210> SEQ ID NO 15
<211> LENGTH: 10
<212> TYPE: PRT
<213> ORGANISM: Artificial Sequence
```

```
<220> FEATURE:
<223> OTHER INFORMATION: Synthesized sequence

<400> SEQUENCE: 15

Lys Lys Leu Arg Ile Lys Gln Lys Glu Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthesized sequence

<400> SEQUENCE: 16

Lys Lys Leu Arg Ile Gln Ser Lys Glu Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthesized sequence

<400> SEQUENCE: 17

Lys Lys Leu Arg Ile Lys Ser Gln Glu Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthesized sequence

<400> SEQUENCE: 18

Lys Lys Leu Arg Ile Lys Ser Lys Glu Gln
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthesized sequence

<400> SEQUENCE: 19

Pro Ser Gly Lys Pro Lys Ser Leu Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized sequence

<400> SEQUENCE: 20

Thr Ser Val Thr Pro Lys Gln Ser Leu
1               5

<210> SEQ ID NO 21
<211> LENGTH: 12
<212> TYPE: PRT
<213> ORGANISM: Artificial Sequence
```

```
<220> FEATURE:
<223> OTHER INFORMATION: Synthesized sequence

<400> SEQUENCE: 21

Asn Ser Phe Met Ala Leu Tyr Leu Ser Lys Gly Arg
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthesized sequence

<400> SEQUENCE: 22

Ala Lys Leu Arg Ile Lys Ser Lys Glu Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthesized sequence

<400> SEQUENCE: 23

Lys Lys Leu Ala Ile Lys Ser Lys Glu Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthesized sequence

<400> SEQUENCE: 24

Lys Lys Leu Arg Ile Lys Ala Lys Glu Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthesized sequence

<400> SEQUENCE: 25

Lys Lys Leu Arg Ile Gln Ser Gln Glu Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthesized sequence

<400> SEQUENCE: 26

Lys Lys Leu Arg Ile Lys Ser Gln Glu Gln
1               5                   10

<210> SEQ ID NO 27
<211> LENGTH: 10
<212> TYPE: PRT
<213> ORGANISM: Artificial Sequence
```

```
<220> FEATURE:
<223> OTHER INFORMATION: Synthesized sequence

<400> SEQUENCE: 27

Lys Lys Leu Arg Ile Gln Ser Lys Glu Gln
 1               5                  10

<210> SEQ ID NO 28
<211> LENGTH: 10
<212> TYPE: PRT
<213> ORGANISM: Artificial Sequence
<220> FEATURE:
<223> OTHER INFORMATION: Synthesized sequence

<400> SEQUENCE: 28

Lys Lys Leu Arg Ile Gln Ser Gln Glu Gln
 1               5                  10

<210> SEQ ID NO 29
<211> LENGTH: 10
<212> TYPE: PRT
<213> ORGANISM: Artificial Sequence
<220> FEATURE:
<223> OTHER INFORMATION: Synthesized sequence

<400> SEQUENCE: 29

Gln Gln Leu Arg Ile Lys Ser Lys Glu Lys
 1               5                  10

<210> SEQ ID NO 30
<211> LENGTH: 7
<212> TYPE: PRT
<213> ORGANISM: Artificial Sequence
<220> FEATURE:
<223> OTHER INFORMATION: Synthesized sequence

<400> SEQUENCE: 30

Arg Ile Lys Ser Lys Glu Lys
 1               5

<210> SEQ ID NO 31
<211> LENGTH: 10
<212> TYPE: PRT
<213> ORGANISM: Artificial Sequence
<220> FEATURE:
<223> OTHER INFORMATION: Synthesized sequence

<400> SEQUENCE: 31

Lys Lys Leu Lys Ile Arg Ser Gln Glu Lys
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Synthesized sequence

<400> SEQUENCE: 32

Phe Lys Lys Arg Thr Lys Ser Lys Glu Asp
 1               5                  10

<210> SEQ ID NO 33
<211> LENGTH: 12
<212> TYPE: PRT
<213> ORGANISM: Artificial Sequence
```

```
<220> FEATURE:
<223> OTHER INFORMATION: Synthesized sequence

<400> SEQUENCE: 33

Thr Ala Leu Arg Ile Arg Ala Thr Tyr Gly Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthesized sequence

<400> SEQUENCE: 34

Asp Gly Lys Lys Leu Arg Ile Lys Ser Lys Glu Lys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthesized sequence

<400> SEQUENCE: 35

Lys Ser Ile Arg Val Ala Val Ala Pro Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthesized sequence

<400> SEQUENCE: 36

Lys Ser Ile Arg Ile Ala Ile Ala Pro Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthesized sequence

<400> SEQUENCE: 37

Lys Ser Ile Arg Val Gly Val Gly Pro Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthesized sequence

<400> SEQUENCE: 38

Lys Ser Ile Arg Ile Gly Ile Gly Pro Gly
1               5                   10

<210> SEQ ID NO 39
<211> LENGTH: 376
<212> TYPE: PRT
<213> ORGANISM: Artificial Sequence
```

<220> FEATURE:
<223> OTHER INFORMATION: Synthesized sequence

<400> SEQUENCE: 39

```
Asp Thr Pro Val Ala Ser Pro Arg Ser Val Lys Val Trp Gln Asp Ala
1               5                   10                  15
Cys Ser Pro Leu Pro Lys Thr Gln Ala Asn His Gly Ala Leu Gln Phe
            20                  25                  30
Gly Asp Ile Pro Thr Ser His Leu Leu Phe Lys Leu Pro Gln Glu Leu
        35                  40                  45
Leu Lys Pro Arg Ser Gln Phe Ala Val Asp Met Gln Thr Thr Ser Ser
    50                  55                  60
Arg Gly Leu Val Phe His Thr Gly Thr Lys Asn Ser Phe Met Ala Leu
65                  70                  75                  80
Tyr Leu Ser Lys Gly Arg Leu Val Phe Ala Leu Gly Thr Asp Gly Lys
                85                  90                  95
Lys Leu Arg Ile Lys Ser Lys Glu Lys Cys Asn Asp Gly Lys Trp His
            100                 105                 110
Thr Val Val Phe Gly His Asp Gly Glu Lys Gly Arg Leu Val Val Asp
        115                 120                 125
Gly Leu Arg Ala Arg Glu Gly Ser Leu Pro Gly Asn Ser Thr Ile Ser
    130                 135                 140
Ile Arg Ala Pro Val Tyr Leu Gly Ser Pro Pro Ser Gly Lys Pro Lys
145                 150                 155                 160
Ser Leu Pro Thr Asn Ser Phe Val Gly Cys Leu Lys Asn Phe Gln Leu
                165                 170                 175
Asp Ser Lys Pro Leu Tyr Thr Pro Ser Ser Ser Phe Gly Val Ser Ser
            180                 185                 190
Cys Leu Gly Gly Pro Leu Glu Lys Gly Ile Tyr Phe Ser Glu Glu Gly
        195                 200                 205
Gly His Val Val Leu Ala His Ser Val Leu Leu Gly Pro Glu Phe Lys
    210                 215                 220
Leu Val Phe Ser Ile Arg Pro Arg Ser Leu Thr Gly Ile Leu Ile His
225                 230                 235                 240
Ile Gly Ser Gln Pro Gly Lys His Leu Cys Val Tyr Leu Glu Ala Gly
                245                 250                 255
Lys Val Thr Ala Ser Met Asp Ser Gly Ala Gly Gly Thr Ser Thr Ser
            260                 265                 270
Val Thr Pro Lys Gln Ser Leu Cys Asp Gly Gln Trp His Ser Val Ala
        275                 280                 285
Val Thr Ile Lys Gln His Ile Leu His Leu Glu Leu Asp Thr Asp Ser
    290                 295                 300
Ser Tyr Thr Ala Gly Gln Ile Pro Phe Pro Ala Ser Thr Gln Glu
305                 310                 315                 320
Pro Leu His Leu Gly Gly Ala Pro Ala Asn Leu Thr Thr Leu Arg Ile
            325                 330                 335
Pro Val Trp Lys Ser Phe Phe Gly Cys Leu Arg Asn Ile His Val Asn
        340                 345                 350
His Ile Pro Val Pro Val Thr Glu Ala Leu Glu Val Gln Gly Pro Val
    355                 360                 365
Ser Leu Asn Gly Cys Pro Asp Gln
370                 375
```

PEPTIDE PROMOTING CELL ADHESION AND MIGRATION

This application is a national stage application under 35 U.S.C. §371 of PCT Application No. PCT/FR2010/050458, filed Mar. 15, 2010, which claims priority to and the benefit of French patent application no. 0901168, filed Mar. 13, 2009, which is incorporated herein by reference in its entirety.

The invention concerns a new peptide with a defined sequence present in the alpha3 chain of the LG4 globule of laminin 332 (laminin 5), and peptides with sequences homologous to the said peptide with the defined sequence capable of binding to the syndecan-1 receptor. It also concerns a pharmaceutical or cosmetic composition containing the said peptide. Finally it concerns the use of the peptide in the area of tissue healing and regeneration or as an adjuvant in culture media intended for epidermal or epithelial reconstruction.

Each year tens of millions of patients suffer tissue loss or organ deficiencies. Although transplantation of the organs and tissues concerned meets part of the demand, this therapeutic approach is greatly limited by the lack of donors and by the potential rejection of allografts which requires long-term immunosuppressant treatment.

Over the last ten years or so, interest in tissue engineering has grown incredibly fast both in terms of fundamental research and in terms of defining and developing "artificial tissues" which are beginning to be offered for clinical applications by various companies. Tissue engineering is a multi-disciplinary area applying engineering and life science principles to the development of biological substitutes with the aim of restoring, maintaining or improving a tissue function.

Tissue engineering associates biodegradable natural and synthetic biomaterials, undifferentiated cells (stem cells) or differentiated cells (keratinocytes, fibroblasts, chondrocytes etc.) and (or) active molecules such as growth factors or adhesion molecules. Indeed, cell adhesion is an essential and decisive step for successfully implanting biomaterials in the human body. While this has been improved by the development of highly interactive surfaces, it nevertheless remains dependent on the presence of matrix adhesion proteins, or on their synthesis by the cells.

Moreover, 5 million people annually need healing dressings to treat difficult lesions (eschars and leg ulcers). Many dressing which are supposed to promote the healing of the skin are currently on the market and research in this area is on the increase. Despite the efforts made in the treatment and prevention of infection and dehydration, there are still many problems concerning management of complicated healing problems. Indeed, the problem of healing chronic lesions will increase due to increasing life expectancy and ageing of populations. A new era is in prospect with the development of dressings containing adhesion molecules.

Skin healing is a complex phenomenon in which dermal and epidermal events are closely implicated. It is not, as was thought for a long time, a simple linear process during which growth factors are synthesised to activate cell proliferation and migration. On the contrary, it is the result of several dynamic and interactive processes bringing into play soluble factors, components of the blood and of the extracellular matrix (ECM) and parenchyma and epithelial cells (Clark, 1996).

Interaction between the cells and the ECM plays a role in organising cell behaviour by controlling the expression of certain genes, or by modulating migration, proliferation, differentiation or programmed cell death (Hynes, 1992). This control of cellular behaviour is crucial during tissue reshaping. When there is a skin wound, the dermo-epidermal junction (DEJ) is damaged and the molecules constituting it are destroyed or broken down by specific enzymes. The dermis plays a fundamental role during re-epithelialisation by producing soluble factors for the epithelial cells and informative matrix molecules with which the keratinocytes are in direct contact. Under favourable conditions, epidermal re-epithelialisation begins a few hours after the trauma. The inflammatory reaction causes the appearance of matrix molecules on the bed of the wound, on to which the keratinocytes from residual epithelial structures rapidly migrate.

During the repair process, the migrating keratinocytes lose their apical-basal polarity, adhere to the provisional matrix, and form pseudopodia which allow them to migrate laterally (Larjava et al., 1993). When the epithelium has covered the wound bed, the DEJ proteins reappear in a sequential, ordered manner from the edges of the wound extending towards the centre. The basal keratinocytes then readopt a stationary phenotype with apical polarity, firmly anchored to the DEJ via the hemidesmosomes (HDs) reformed on their basal surface. Migration and adhesion of the basal keratinocytes is controlled by specific interactions between certain peptide motifs present on the matrix molecules and trans-membrane receptors, grouped into adhesion complexes, the intracellular domain of which is linked to constituents of the cytoskeleton (Aumailley et al., 1996). Cell adhesion complexes are large multimolecular aggregates allowing bidirectional transfer of information across the cell membrane. These complexes, consisting of extracellular, transmembrane (integrins and syndecans), cytosolic and cytoskeletal proteins, are highly dynamic structures, stabilised in a more or less transitory fashion by specific interactions between the various constituents. Assembly and disassembly of adhesion complexes are finely regulated to allow the cell to perform key operations such as adhesion, migration, proliferation and differentiation.

In the wide range of extracellular ligands, laminin 332 (LN332), also known as laminin 5 plays a fundamental role in both these processes (Aumailley and Rousselle, 1999; Ghohestani et al., 2001). This adhesion molecule has two functions: with finely controlled regulation, it is capable of inducing strong, static cell adhesion or, conversely, low affinity adhesion allowing transitory cell migration. This property is very well illustrated in the skin as LN332 is responsible for anchoring the epidermis and is also involved in keratinocyte migration during the healing process.

LN332 consists of an assembly of 3 subunits: alpha3, beta3 and gamma2 (FIG. 1). It is the main, irreplaceable adhesion protein in the epidermis where it was identified as the major component of anchoring filaments, structures that connect the HDs to the basal part of the DEJ in the skin (Rousselle et al., 1991). It is involved in the adhesion of many other epithelial cells of the body (Rousselle and Aumailley, 1994). It is exclusively synthesised by the epithelial cells as a 460 kDa precursor (pre-LN332). The alpha3 chain which is longer than the other 2 has at its carboxy-terminal end a globular domain consisting of 5 repetitions of basic residues appearing as 5 globules called LG1 to LG5 (LG1-2-3-4-5). These globular domains are very important since they include the domains responsible for keratinocyte adhesion.

The document WO2000/66731 describes the production of whole laminin 5 in a recombinant form.

Document WO2006/018551 describes the involvement of the TALRIRATYGEY (SEQ ID NO: 33) sequence present on the gamma2 chain of the N-terminal end of laminin 5 in epidermal keratinocyte adhesion.

In this application, the applicant is interested in the carboxy-terminal end of the alpha3 chain of pre-LN332.

Under physiological conditions, each of the alpha3 and gamma2 subunits of LN332 undergoes extracellular post-translational cleavage of its carboxy-terminal and amino-terminal end respectively (Marinkovich et al., 1994; Goldfinger et al., 1998; Amano et al., 2000). This differing cleavage results in the mature forms which play a crucial role in epithelial-mesenchymal cohesion both on the supra-molecular organisation level at the amino-terminal ends and as regards cell interactions brought about by the LG domains (Aumailley and Rousselle, 1999). Maturation of the alpha3 chain, which results from splitting the LG4/5 tandem, induces determinant functional changes in the LN332, as it allows adhesion of adjacent epithelial cells via alpha6beta4 integrins, and assembly of stable adhesion structures, the hemidesmosomes (Sonnenberg et al., 1993; Rousselle et Aumailley, 1994; Niessen et al., 1994). Mature LN332 would thus be a barrier to cell motility (Baker at al.; 1996; Goldfinger et al., 1998; Ryan et al., 1999). However, pre-LN332 is capable, through the LG4/5 globules of the alpha3 chain precursor, of preventing the formation of hemidesmosomes and inducing cell migration (Ryan et al., 1999; Goldfinger et al., 1999; Bachy et al., 2008). In vivo studies of skin healing have shown increased expression of the various LN332 chains by keratinocytes in the wound colonisation area (Ryan et al., 1994), LN332 being present in the extracellular matrix in its precursor form (Ryan et al., 1994; Lampe et al., 1998; Nguyen et al., 2000). Pre-LN332 is thus present in the provisional matrix but is totally absent in the organised basal lamina where it appears in its matured form (Lampe et al., 1998; Goldfinger et al., 1999; Tungall et al., 2002). Moreover, while in vitro studies very soon reported over-expression and increased synthesis of LN332 by mobile keratinocytes (Rousselle et al., 1991), its involvement via the precursor form was only found much later (Nguyen et al., 2000; Décline and Rousselle, 2001). All these data show that the LG4/5 domain influences cell migration and plays a role in the epithelial repair process. Work including that of the inventors of this application has shown that pre-LN332 cooperates with alpha3beta1 integrin to control cell polarisation and migration (Goldfinger et al., 1998; Décline and Rousselle, 2001; Frank and Carter, 2004; Bachy et al., 2008). In addition, a study suggests a role for the LG4/5 fragment in the deposition and retention of pre-LN332 in the extracellular matrix (Sigle at al., 2004).

Finally, it has been shown that the LG4/5 domain of pre-LN332 interacts with a receptor belonging to the proteoglycan family, syndecan-1, during keratinocyte migration (Okamoto et al., 2003; Bachy et al., 2008).

In the epidermis, syndecan-1 is localised in the pericellular region of the keratinocytes of the suprabasal layers and is expressed little in the basal layer. Remarkably, the expression of syndecan-1 is strongly activated during wound healing and is primarily localised at the edges of wounds (Elenius et al., 1991; Oksala et al., 1995; Jaakkola et al., 1998). This expression pattern is specific to syndecan-1 since it has not been found for the other syndecans (Gallo et al., 1996). Moreover, mice deficient in the gene encoding syndecan-1 have defects in proliferation and migration of keratinocytes during wound healing (Stepp et al, 2002). Syndecans are known to be involved in cell processes such as migration and are also known to be co-receptors, cooperating with integrins and growth factors (Bernfield et al., 1999; Woods et al., 2000). All of these points support the hypothesis that the LG4/5 domain of pre-LN332 is a preferential ligand for syndecan-1 during wound healing and the basis for an intracellular signalling cascade promoting the process of epithelial repair.

The cleavage site of the LG4/5 fragment on the alpha3 chain has been determined (Décline et al., 2003) and the LG4/5 fragment has been produced in recombinant form (Okamoto et al., 2003). Cell adhesion and migration experiments carried out with the LG4/5 fragment have shown that this domain is involved in cell migration and that a membrane receptor, syndecan-1, is specifically involved in its recognition (Okamoto et al., 2003, Bachy et al., 2008). The syndecans belong to a family of membrane receptors with chains of heparan sulphate expressed on the surface of all the adhering cells. These receptors have been described as molecular 'facilitators' capable of modulating integrin activity via intracellular signalling linked to the cytoskeleton. Cell adhesion to the LG4/5 fragment depends on the chains of heparan sulphate and chondroitin sulphate present on syndecan-1. While these two chains of glycosaminoglycans bind to the LG4/5 fragment with differing affinity, they recognise the same interaction domain in the LG4/5 globule (Okamoto et al., 2003). Pre-LN332 induces migration of normal human keratinocytes through syndecan-1 interacting with the LG4/5 domain. Syndecan-1 dependent adhesion to the LG4/5 domain of pre-LN332 induces reorganisation of the normal human keratinocyte cytoskeleton leading to the formation of filopodia and microspicules, cytoplasmic protrusions which are characteristic of cell migration. This early stage is accompanied by activation of the GTPases Rac and Cdc42, GTPases known to be involved in the formation of transitory adhesion complexes specific to cell migration (Bachy et al., 2008).

With determination of the structure of the LG5 module of the alpha2 chain of LN211 (Tisi et al., 2000; Timpl et al., 2000), a basic structural model could be made of these LG modules, which are organised in the form of 14 beta lamellae (A to N) connected to one another by loops directed to the outside of the structure. Using technology based on the covalent bonding of the recombinant LG4/5 fragment onto heparin coated beads followed by enzymatic fragmentation of the protein, three sequences corresponding to 'heparin-binding zones' have been identified (Vives et al., 2004), respectively the sequences KKLRIKSKEK (SEQ ID NO: 1), PSGKPKSLP (SEQ ID NO: 19) and TSVTPKQSL (SEQ ID NO: 20). In this document, experiments were conducted using the native protein and binding sites were identified without their having been isolated in the peptide state.

The documents JP2006063033 and Utani et al, 2001 at the same time described the NSFMALYLSKGR (SEQ ID NO: 21) sequence (from residue 1412 to residue 1423 of the sequence of the alpha3 chain) located in the LG4 module, as inducing cell adhesion via syndecans-2 and -4.

The applicant has demonstrated that the sequence KKLRIKSKEK (SEQ ID NO: 1) (from residue 1433 to residue 1442 of the sequence of the alpha3 chain located in a loop connecting the beta F and G lamellae in the LG4 globule) is the binding site to syndecan-1 in the LG4 module since (1) it alone is capable of inducing syndecan-1 dependent cell adhesion and (2) it is capable of specifically binding syndecan-1 and in a manner equivalent to the whole LG4/5 domain.

The identification of so small a functional peptide was far from obvious, as the document by Urushibata et al demonstrated (Biochemistry, 2009, 48, 10522-10532). In this document the authors analysed the biological activity of 107 synthetic peptides belonging to the G domain of the laminin alpha3 chain, without bringing to light the one which is the subject of this invention.

The invention therefore primarily concerns a synthetic or analogous peptide including the sequence KKLRIKSKEK (SEQ ID NO: 1) or a sequence of identical size, in which the K residue (in position 1) and the R residue (in position 4) are conserved, the sequence being able to bind to the syndecan-1 receptor.

As concerns the peptides of interest, where the sequence SEQ ID NO: 1 itself or a sequence containing SEQ ID NO: 1 has already been described, the invention focuses advantageously on the functional variants of this sequence. Thus, in a preferred embodiment, the invention relates to synthetic peptides containing or consisting of the sequence $Kaa_2aa_3Raa_5aa_6aa_7aa_8aa_9aa_{10}$, the sequence being capable of binding to the syndecan-1 receptor, with the exception of peptides containing or consisting of the sequence KKLRIKSKEK (SEQ ID NO: 1). However, for therapeutic applications, it is considered that all the peptides, including those containing or consisting of sequence SEQ ID NO: 1 are concerned.

The document US 2005/0059602 in fact describes sequence A3G78 consisting of 12 aa and including SEQ ID NO: 1. More specifically, the following peptides are therefore excluded:

```
KKLRIKSKEK;            (SEQ ID NO: 1)
DGKKLRIKSKEK.          (SEQ ID NO: 34)
```

The document by Hashimoto et al. (Biomaterials 25 (2004), 1407-1414) describes hybrid peptides associated with alginate dressings. Some have a size of 10 aa, with an arginine residue (R) in position 4. However, these peptides have an acetyl-lysine (ac-K) in position 1 and cannot bind to the syndecan-1 receptor. Therefore the following peptides are also not covered by this invention:

```
Ac-KSIRVAVAPG          (SEQ ID NO: 35)
Ac-KSIRIAIAPG          (SEQ ID NO: 36)
Ac-KSIRVGVGPG          (SEQ ID NO: 37)
Ac-KSIRIGIGPG.         (SEQ ID NO: 38)
```

Binding to syndecan-1 can be easily shown by any technique known to those working in the field, in particular by affinity chromatography. A test of this type can for example consist of fixing the peptide to be tested onto beads, then incubating them with keratinocyte lysates. The cell proteins thus fixed onto the peptide can then be analysed by SDS PAGE electrophoresis followed by immunodetection to evaluate the syndecan-1 content.

In the rest of the description it is shown using quantitative analysis that cell adhesion revealed by the KKLRIKSKEK peptide (SEQ ID NO: 1) is more effective than adhesion revealed by the NSFMALYLSKGR (SEQ ID NO: 21) peptide, firstly because the cell adhesion is induced by a smaller amount of immobilised peptide and secondly, the total number of adherent cells is greater by 200% on the KKLRIKSKEK (SEQ ID NO: 1) peptide regardless of the amount of peptide immobilised.

In the rest of the description and in the claims, the term 'peptide analogue' means the peptide of the invention in a modified form provided that the said peptide retains its ability to bind to syndecan-1. The modifications may be conformational. The peptide may therefore be in an oligomerised, folded or cyclised form. The modifications may also be chemical, so that a peptide, for example, onto which a motif of interest is grafted or the side chain of which is chemically modified is also covered by this invention In a particular embodiment, the peptide of the invention contains at most 30 amino acids, preferably at most 18 amino acids, and contains the sequence KKLRIKSKEK (SEQ ID NO: 1).

In another embodiment, the peptide consists of the sequence KKLRIKSKEK (SEQ ID NO: 1) or a sequence of identical size, in which the K residue (position 1) and R residue (position 4) are conserved.

In a particular embodiment, the peptide of the invention contains or consists of the sequence $aa_1aa_2aa_3aa_4aa_5aa_6aa_7aa_8aa_9aa_{10}$ in which, at physiological pH:

$aa_1$ is a lysine residue,
$aa_4$ is an arginine residue,
$aa_2$, $aa_6$, $aa_8$, $aa_{10}$ are positively charged residues; at the most one of them may be substituted by a neutrally charged residue,
$aa_3$ is a neutrally charged residue,
$aa_5$ is a neutrally charged residue,
$aa_7$ is a neutrally charged residue with the exception of alanine,
$aa_9$ is a negatively or neutrally charged residue.

In other words, the peptide of the invention contains or consists of the sequence $Kaa_2aa_3Raa_5aa_6aa_7aa_8aa_9aa_{10}$ in which, at physiological pH:

$aa_2$, $aa_6$, $aa_8$, $aa_{10}$ are positively charged residues; at the most one of them may be substituted by a neutrally charged residue,
$aa_3$ is a neutrally charged residue,
$aa_5$ is a neutrally charged residue,
$aa_7$ is a neutrally charged residue with the exception of alanine,
$aa_9$ is a negatively or neutrally charged residue.

In the rest of the description and the claims, a neutrally charged residue denotes the following amino-acids: phenylalanine, methionine, tryptophan, valine, leucine, isoleucine, alanine, proline, glycine, cysteine, asparagine, glutamine, serine, threonine and tyrosine.

Similarly, a positively charged residue denotes the following amino acids: lysine, arginine and histidine.

Finally, a negative charged residue denotes the following amino acids: aspartic acid, glutamic acid.

The applicant has obtained very good cell adhesion results with the peptides containing or consisting of the following sequences:

```
A2:    KALRIKSKEK     (SEQ ID NO: 2)
A3:    KKARIKSKEK     (SEQ ID NO: 3)
A5:    KKLRAKSKEK     (SEQ ID NO: 4)
A6:    KKLRIASKEK     (SEQ ID NO: 5)
A8:    KKLRIKSAEK     (SEQ ID NO: 6)
A9:    KKLRIKSKAK     (SEQ ID NO: 7)
A10:   KKLRIKSKEA     (SEQ ID NO: 8)
M2:    KKLRLRSKER     (SEQ ID NO: 9)
M4:    KKLRHKSKEK     (SEQ ID NO: 10)
M5:    KKLRTKSKEK     (SEQ ID NO: 11)
M6:    KKLRKKSKEK     (SEQ ID NO: 12)
M7:    KKLRSKSKEK     (SEQ ID NO: 13)
M8:    KKLRIKLKEK     (SEQ ID NO: 14)
M9:    KKLRIKQKEK     (SEQ ID NO: 15)
```

```
-continued
U1:        KKLRIQSKEK       (SEQ ID NO: 16)

U2:        KKLRIKSQEK       (SEQ ID NO: 17)

U3:        KKLRIKSKEQ.      (SEQ ID NO: 18)
```

The invention also relates to the use of a synthetic peptide sequence containing or consisting of the peptide defined above as a medicinal product or for the manufacture of a pharmaceutical composition or a medical device advantageously intended to improve healing of the skin, in particular following skin disease or trauma.

The skin conditions concerned are particularly:
Ulcers, eschars
Treatment of the skin after dermatological procedures, for example for aesthetic purposes to treat aging, melasma, $CO_2$ or Erbium laser treatment, fractional laser, chemical peel, microdermabrasion,
Diseases of the dermo-epidermal junction, e.g. epidermolysis bullosa,
Psoriasis.

The traumas concerned are in particular:
Superficial to deep second degree burns, third degree burns, dermal abrasion, blisters
Dermal reconstruction, plastic surgery, skin grafts
Skin graft donor sites The peptide according to the invention can also be used for tissue regeneration, particularly for repulping or rethickening the skin. In this context, it is of interest for filling wrinkles for example.

The invention also concerns a pharmaceutical or cosmetic composition containing the peptide described above which may take several forms.

In a first embodiment, the pharmaceutical composition of the invention is more like a medical device, in this case a support onto which the synthetic peptide of the invention is grafted or deposited, or within which it is incorporated, the support being in the form of a film or a matrix consisting of a biological material selected from the group consisting of collagen, gelatine, polysaccharide, hyaluronic acid, cellulose, carboxymethylcellulose, pectin, chitosan, human or animal acellular dermis, or a synthetic material selected from the group consisting of silicone, polyurethane, PLLA, or textile dressing material selected from the group including cotton, polyester and polyamide.

Such devices are notably used for the reconstruction of skin in third degree burns. The invention therefore also concerns a skin reconstruction process, especially in third degree burns, consisting of applying the medical device described above in contact with the skin.

In a second embodiment, the pharmaceutical or cosmetic composition of the invention is in the form of a cream, a hydrogel, a solution, an injectable formulation or a spray which may include autologous keratinocytes or mesenchymal cells.

In the case of the solution, cream or hydrogel, the peptide or peptides are incorporated into these preparations which are intended, for example, to be brushed onto the skin during a skin graft at the donor and recipient sites of the epidermal or dermo-epidermal grafts and also used in healing the skin after grazing, second degree burns, in chronic lesions or in any medical procedures treating the epidermis.

In another application, the peptide or peptides are incorporated into an injectable formulation for treating skin aging, for example, mesotherapy. Topical application may also be envisaged.

The spray form is particularly suitable for applications in tissue engineering before placing epidermal lamellae or total autologous or allogeneic skin, for example for the treatment of major burns or healing recalcitrant wounds such as ulcers. In a particular embodiment, in addition to the peptide the spray form may also contain autologous keratinocytes. The treatment performed particularly in major burn cases can be carried out in one or two stages.

Single Stage Treatment:
A skin flap is removed followed by enzymatic digestion of this tissue, then a cell suspension is recovered to which the peptide or peptides are added. The cell/peptide mixture is then sprayed onto the wound to be treated.

Two Stage Treatment:
A skin flap is removed followed by enzymatic digestion of the epidermal flap. The keratinocytes are isolated and then cultured for amplification. The cells are recovered as a suspension to which the peptide or peptides are added. The mixture is then sprayed onto the wound to be treated.

The invention also concerns a culture medium containing the peptide described above, for in vitro culture of epithelial or mesenchymal cells.

More precisely, the peptide or peptides can be added to specific culture media for the in vitro culture of epithelial or mesenchymal cells (keratinocytes and fibroblasts, among others) either directly into the culture medium during manufacture or as a supplement added extemporaneously to the culture medium during use.

Such a culture medium may be for culturing keratinocytes and other epithelial cells (corneal epithelium, buccal or vaginal epithelium) for medical, scientific, research or pharmaco-toxicological applications, the addition of the peptide or peptides being to facilitate and/or shorten the culture stages, and/or improve the quality of the cultures and cell construction (cell layers, pseudoepidermis, reconstructed epithelia).

A typical keratinocyte culture medium is described for example in the U.S. Pat. No. 5,654,135.

Applications of epithelial cell or keratinocyte cultures include for example:
Producing an epidermis or reconstructed epithelium for testing cosmetic or pharmacological molecules or pharmacological or cosmetic preparations (without using animal models)
In the treatment of major burns victims or treating wound healing (e.g. varicose ulcers and diabetic ulcers), by spraying cells or epidermal lamellae. The peptide of the invention may also be used in a culture medium for normal human keratinocytes intended to keep skin substitutes viable before grafting, especially for a major burns victim.
For the purposes of research, gene therapy, studying keratinocytes, testing new active substances, growth factors etc.
For building cell banks.

The culture medium containing the peptide or peptides may be intended for culturing fibroblasts in vitro to produce whole skins, both prior to keratinocyte seeding and then in the phases producing the pseudo-epidermis. The peptide or peptides allow better adhesion and spread of the fibroblasts, thus limiting the loss of fibroblasts immediately after seeding, and greater mobility of the seeded fibroblasts.

The time required to obtain a good quality dermal equivalent is reduced and a whole skin can be obtained more rapidly.

In vivo, owing to the presence of the peptide within the three-dimensional matrix there is better adhesion and spread of the fibroblasts and the formation of granulation tissue during cutaneous healing is limited.

The invention also concerns a support containing the peptide for the culture of epithelial cells such as keratinocytes. The supports may be in the form of membranes or matrices which can be used to produce a pseudo-epidermis or whole skin that can be used for toxicological testing of products, molecules or cosmetic or pharmaceutical formulations.

The peptide or peptides can reduce losses on seeding, increase the speed of epidermal reconstruction and improve the structural quality of the reconstructed epidermis.

More specifically, the culture support may be polystyrene culture dishes onto which the peptides are adsorbed or grafted.

The culture support may also be a membrane or biopolymer film used for the reconstruction of skin equivalents, such as a membrane of type I and type IV collagen, onto which are the peptides are adsorbed or grafted.

In applications where the peptide is grafted onto the surface of a film, matrix, membrane or cell culture dish, a group can be added to the C or N-terminal part to allow covalent bonding to the support. This group reacting with the support may be separated from the peptide by a spacer arm.

The group may consist for example of grafting the Cys-Gly-Gly motif onto the N-terminal part for a reaction with chloroacetyl chitosan as described by Masuda et al. (2009).

A biotin arm may also be added allowing non-covalent grafting onto an avidin functionalised support.

The culture support may also be in the form of a textile membrane or porous matrix onto which the peptides are adsorbed or grafted.

The culture support may also be in the form of gels, for example acid-soluble collagen gels onto which the peptides are adsorbed or grafted.

The peptide or peptides may also be added irrespective of the culture medium as a coating solution, e.g. for coating a culture dish or a biopolymer membrane used to reconstruct skin equivalents, e.g. a membrane of type I and type IV collagen.

The invention and the advantages resulting from it are illustrated well by the examples with the figures attached.

FIG. 1: Representation of laminin 332

The alpha3, beta3 and gamma2 chains are assembled to form a supercoiled alpha helix at their C-terminal ends. The alpha3 chain, which is longer than the other two, has at its C-terminal end a series of five globular domains LG1 to LG5. The molecule is organised into domains: LN (laminin N-terminal domain), LE (laminin epidermal growth factor like domain), L4 (laminin domain 4), LG (laminin globular domain), LCC (laminin coiled-coil).

FIG. 2: Peptide sequence of the LG4/5 domain and location of the syndecan-1 binding site (SEQ ID NO: 39).

Sequence of the LG4/5 domain of the alpha3 chain of pre-LN332. The N-terminal sequence starts from the aspartic acid cleavage site in position 1338 and ends with glutamic acid in position 1713. The regions underlined represent linear 'spacer' domains between the globules. The syndecan-1 binding domain KKLRIKSKEK (SEQ ID NO: 1) is shown in bold black, position 1433 to position 1442.

Figure 3:
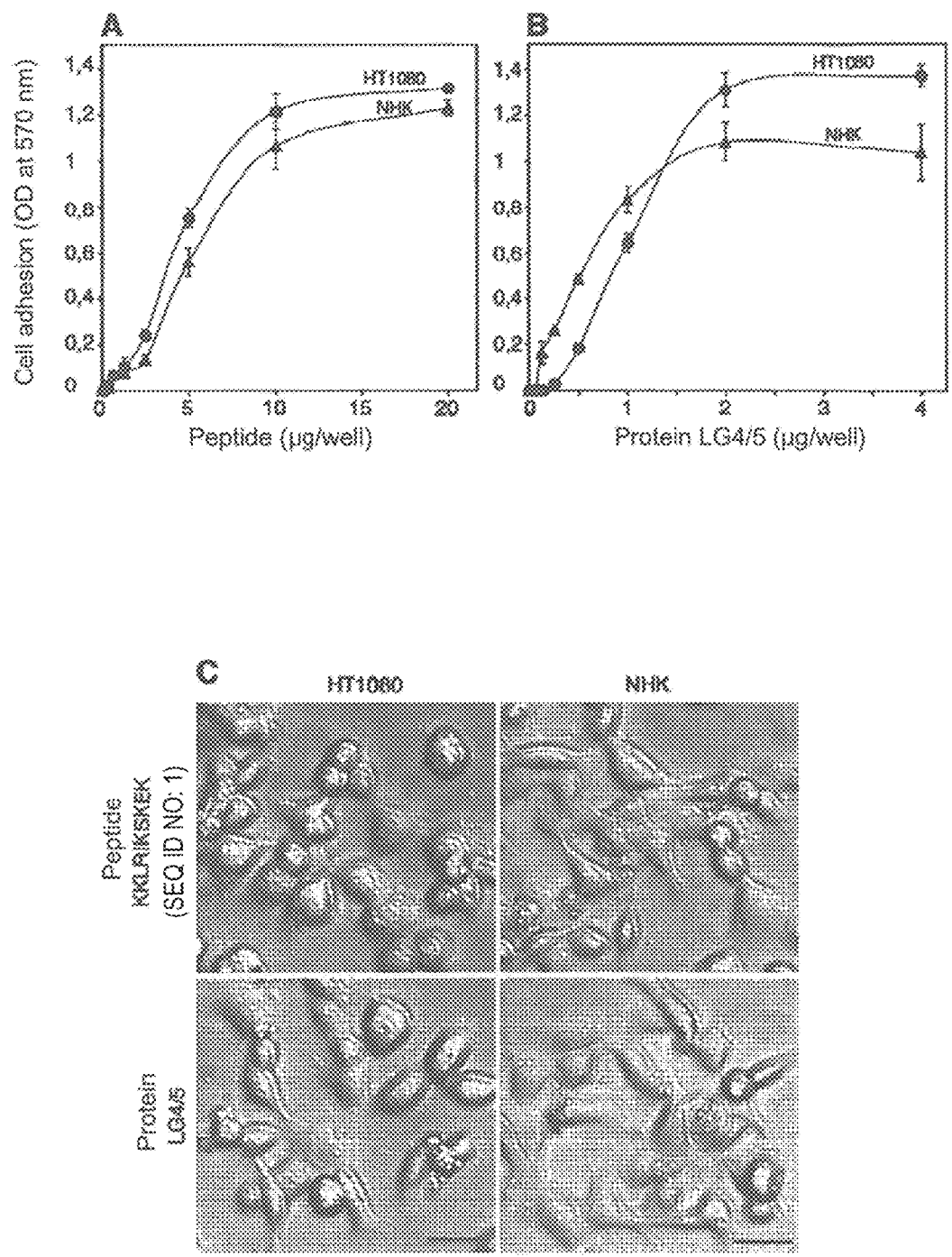

FIG. 3: Adhesion of normal human keratinocytes and HT1080 cells to the LG4/5 fragment and to the peptide KKLRIKSKEK (SEQ ID NO: 1).

(A, B) Dose-dependent adhesion of normal human keratinocytes and cells of the HT1080 strain to the peptide KKLRIKSKEK (SEQ ID NO: 1) and to the LG4/5 protein. The peptide (A) and the protein LG4/5 (B) were immobilised on 96-well plates at the concentrations indicated on the abscissa. $6 \cdot 10^4$ cells were deposited in each well and the plates were incubated at 37° C. for 1 hour. After washing, the adherent cells were fixed and cell adhesion was measured as described in the methodology section. (C) Observation of normal human keratinocytes and HT1080 cells adhering to KKLRIKSKEK peptide (SEQ ID NO: 1) and to the LG4/5 protein. The observation was made with a Zeiss Axiovert 40 microscope equipped with a PlasDic interference unit. 50 μm bar.

Figure 4:
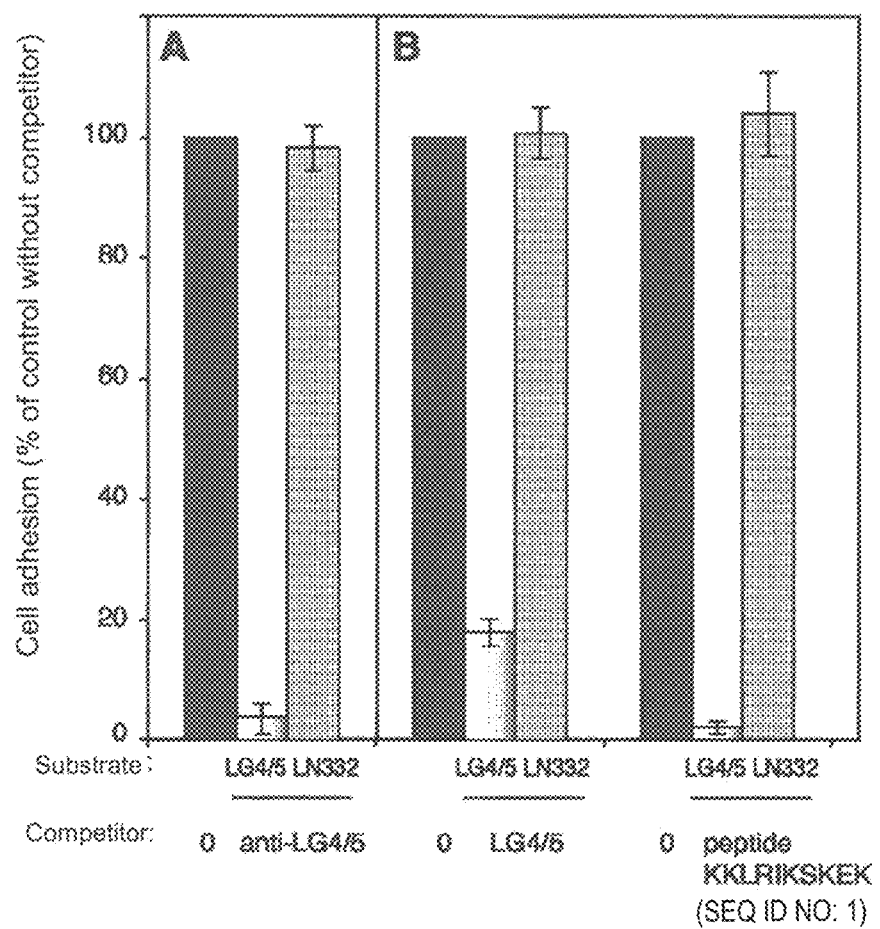

FIG. 4: Effect of the peptide KKLRIKSKEK (SEQ ID NO: 1) on adhesion of cells to the LG4/5 fragment and to laminin 332.

The LG4/5 (white bars) and LN332 (grey bars) proteins (1 μg/well) were adsorbed in 96-well plates. (A) Effect of the polyclonal anti-LG4/5 antibody on cell adhesion to the LG4/5 and LN332 protein. After saturating the wells, a solution of anti-LG4/5 antibody (10 μg/ml) was applied for one hour before performing the adhesion test with HT1080 cells ($6 \cdot 10^4$ cells/well). (B, C) Effect of the LG4/5 protein and the peptide KKLRIKSKEK (SEQ ID NO: 1) in solution on syndecan-1 dependent adhesion to the LG4/5 fragment. The HT1080 cells were detached from the dishes and put into the wells ($6 \cdot 10^4$ cells/well) as they were or in the presence of the LG4/5 protein (10 μg/ml) or the peptide KKLRIKSKEK (SEQ ID NO: 1) (20 μg/ml) as indicated on the graph. (A, B, C) The plates were incubated at 37° C. for 1 hour. After washing, the adherent cells were fixed and cell adhesion was measured as described in the methodology section. Cell adhesion in the presence of antibodies or competitor proteins was shown as a percentage of the cell adhesion obtained on the same substrate without competitor.

Figure 5:
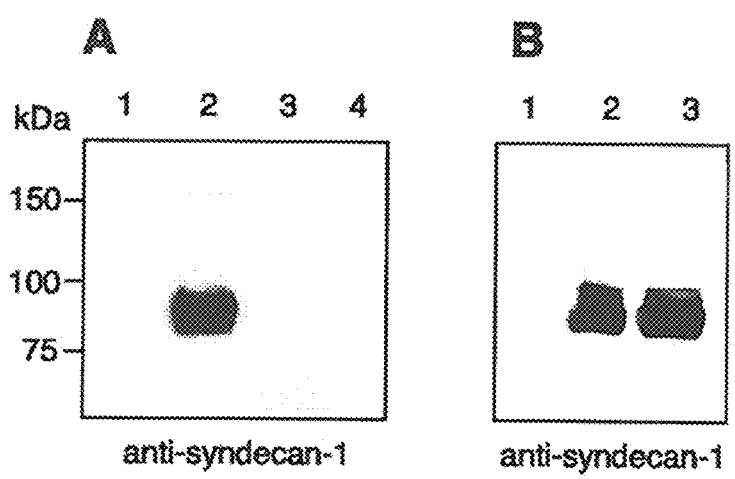

FIG. 5: Demonstration of the specific binding of syndecan-1 to the peptide KKLRIKSKEK (SEQ ID NO: 1) by affinity chromatography.

(A) A lysate of normal human keratinocytes was prepared as described in the Materials and Methods section and 2 mg of the lysate were incubated with neutravidin beads not coated (line 1) or coated with the biotinylated peptides KKLRIKSKEK (SEQ ID NO: 1) (line 2), PSGKPKSLP (SEQ ID NO: 19) (line 3) and TSVTPKQSL (SEQ ID NO: 20) (line 4). After washing, the material bound to the beads was digested with a mixture of heparitinase I and chondroitinase ABC to release the protein part of the syndecan-1 from the glycosaminoglycans. The samples were then analysed by SDS PAGE electrophoresis in an 8% acrylamide gel under non-reducing conditions and by immunoblotting with polyclonal anti-syndecan antibody H174. (B) A lysate of normal human keratinocytes was prepared and 2 mg of the lysate were incubated with neutravidin beads not coated (line 1) or coated with the biotinylated peptide KKLRIKSKEK (SEQ ID NO: 1) (line 3), or with sepharose beads coated with the whole LG4/5 fragment (line 2). After washing, the material bound to the beads was digested with a mixture of heparitinase I and chondroitinase ABC to release the protein part of the syndecan-1 from the glycosaminoglycans. The samples were then analysed by SDS PAGE electrophoresis in an 8% acrylamide gel under non-reducing conditions and by immunoblotting with polyclonal anti-syndecan antibody H174. (A, B) The position of molecular weight markers is shown on the left.

FIG. 6: Adhesion of HT1080 cells to the peptides KKLRIKSKEK (SEQ ID NO: 1) and NSFMALYLSKGR (SEQ ID NO: 21).

(A) A decreasing range of peptides KKLRIKSKEK (SEQ ID NO: 1) and NSFMALYLSKGR (SEQ ID NO: 21) was immobilised in 96-well Microlon plates and the amount actually adsorbed was determined by protein assay with reference to a corresponding range of peptides made extemporaneously. The quantities of peptide tested are indicated on the abscissa of the graph. 6·10⁴ cells were deposited in each well and the plates were incubated at 37° C. for 1 hour. After washing, the adherent cells were fixed and cell adhesion was measured as described in the methodology section. (B) Observation of HT1080 cells adhering to peptides KKLRIK-SKEK (SEQ ID NO: 1) and NSFMALYLSKGR (SEQ ID NO: 21). The observation was made with a Zeiss Axiovert 40 microscope equipped with a PlasDic interference unit. 50 μm bar.

Figure 7:
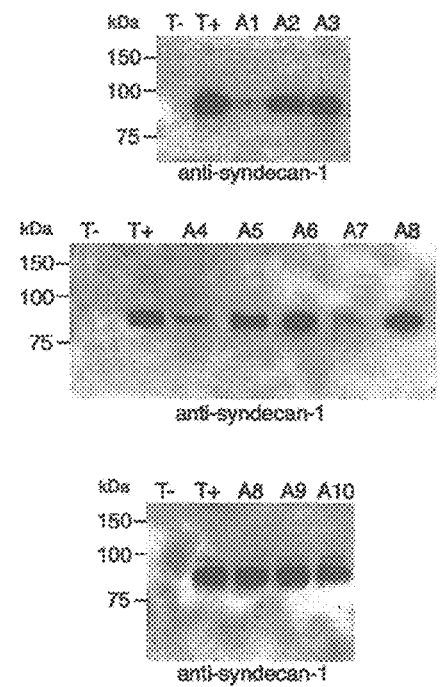

FIG. 7: Peptide KKLRIKSKEK (SEQ ID NO: 1) mutagenesis and its consequence on binding to syndecan-1.

A series of point mutations was introduced into the peptide KKLRIKSKEK (SEQ ID NO: 1) by successively replacing each amino acid by an alanine (A). The different biotinylated mutated peptides are shown in the figure and numbered from A1 to A10. The wild type peptide (T+) is shown in black. The amino acids 'in bold' show the position of the basic amino acids (lysines and arginines) thought to play an important role in the interaction with glycosaminoglycans. Each of the mutations to alanine (A) is highlighted. A lysate of normal human keratinocytes was prepared as described in the Materials and Methods section and 2 mg of the lysate were incubated with neutravidin beads not coated (T−), coated with the peptide KKLRIKSKEK (SEQ ID NO: 1) (T+) or coated with the different mutated peptides (A1 to A10). After washing, the material bound to the beads was digested with a mixture of heparitinase I and chondroitinase ABC to release the protein part of the syndecan-1 from the glycosaminoglycans. The samples were then analysed by SDS PAGE electrophoresis in an 8% acrylamide gel under non-reducing conditions and by immunoblotting with polyclonal anti-syndecan antibody H174. The position of molecular weight markers is shown on the left.

Figure 8:
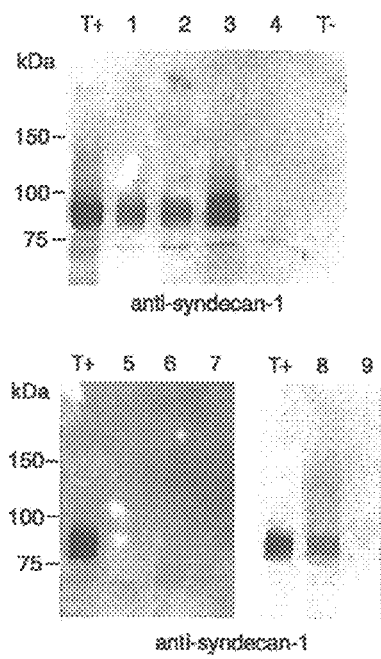

FIG. 8: Peptide KKLRIKSKEK (SEQ ID NO: 1) mutagenesis and its consequence on binding to syndecan-1.

A series of point or multiple mutations was introduced into the peptide KKLRIKSKEK (SEQ ID NO: 1) by replacing one or more lysines (K) by a glutamine (Q). The different biotinylated mutated peptides are shown in the figure and referred to as U1 to U9. The wild type peptide is denoted as T+. The amino acids 'in bold' show the position of the basic amino acids (lysines and arginines) thought to play an important role in the interaction with glycosaminoglycans. Each of the mutations to glutamine (Q), point or multiple, is highlighted. A peptide shortened by 3 residues is shown as U9. A lysate of normal human keratinocytes was prepared as described in the Materials and Methods section and 2 mg of the lysate were incubated with neutravidin beads not coated (line T−), coated with the peptide KKLRIKSKEK (SEQ ID NO: 1) (T+) or coated with the different modified peptides (U1 to U9). After washing, the material bound to the beads was digested with a mixture of heparitinase I and chondroitinase ABC to release the protein part of the syndecan-1 from the glycosaminoglycans. The samples were then analysed by SDS PAGE electrophoresis in an 8% acrylamide gel under non-reducing conditions and by immunoblotting with polyclonal anti-syndecan antibody H174. The position of molecular weight markers is shown on the left.

Figure 9:
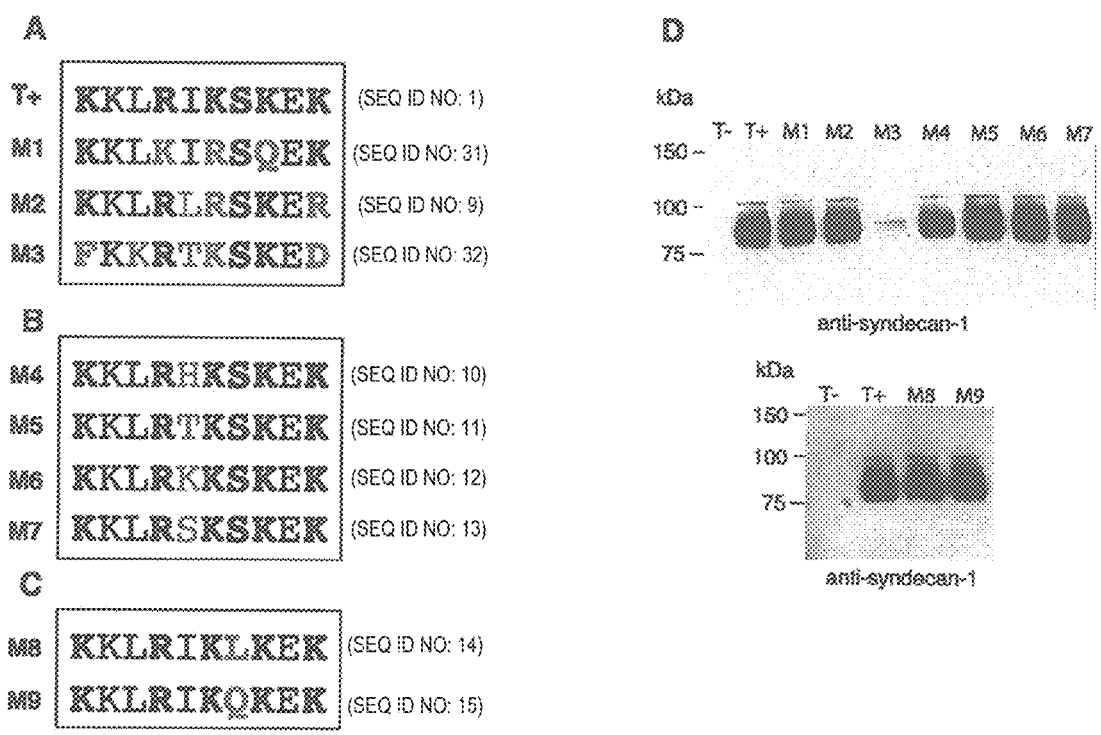

FIG. 9: Mutagenesis of the peptide KKLRIKSKEK (SEQ ID NO: 1) by searching for homologous proteins in the extracellular matrix and the consequence on binding to syndecan-1.

A series of variants of the peptide KKLRIKSKEK (SEQ ID NO: 1) was produced based on sequence homologies found in the extracellular matrix proteins. The wild type peptide is designated as T+. The amino acids 'in bold' represent the position of amino acids playing an important role in the interaction with syndecan-1 (see FIGS. 6 and 7) Amino acids that differ from the original sequence are highlighted. (A) Homologous sequences of the KKLRIKSKEK sequence (SEQ ID NO: 1) were found in the extracellular matrix proteins and were called M1 (from the human and murine laminin alpha4 chain), M2 (from the murine laminin alpha3 chain) and M3 (from human ADAM 20 protein). (B) Homologous sequences of the R-X-KSK sequence were found in the extracellular matrix proteins and were listed as M4 to M7. (C) Homologous sequences of the RIK-X-K sequence were found in the extracellular matrix proteins and were listed as M8 and M9. Lysates of normal human keratinocytes were prepared as described in the Materials and Methods section and 2 mg of the lysate were incubated with neutravidin beads not coated (line T−), coated with the peptide KKLRIKSKEK (SEQ ID NO: 1) (T+) or coated with the different modified peptides (M1 to M9). After washing, the material bound to the beads was digested with a mixture of heparitinase I and chondroitinase ABC to release the protein part of the syndecan-1 from the glycosaminoglycans. The samples were then analysed by SDS PAGE electrophoresis in an 8% acrylamide gel under non-reducing conditions and by immunoblotting with polyclonal anti-syndecan antibody H174. The position of molecular weight markers is shown on the left.

Figure 10:
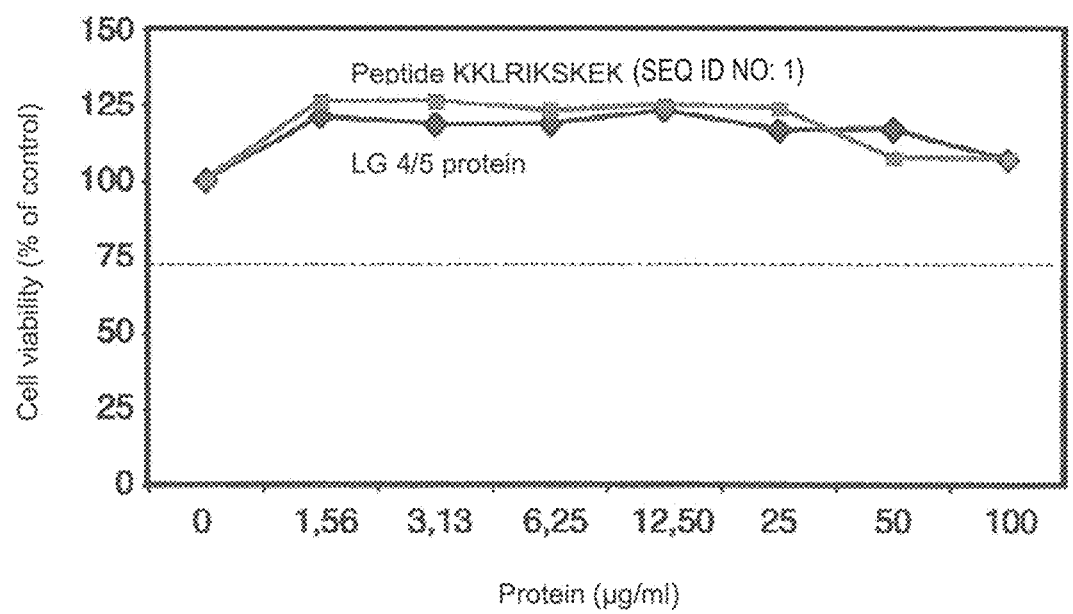

FIG. 10: Effect of the peptide KKLRIKSKEK (SEQ ID NO: 1) on the viability of NHKs.

NHKs were seeded in 96-well plates at 10⁴ cells per well. After 24 hours, the culture media were removed and replaced with KBM-2 medium containing the concentrations of peptide KKLRIKSKEK (SEQ ID NO: 1) (upper curve) or LG4/5 protein (lower curve) shown. After 48 h of contact at 37° C. the media were removed and this step was repeated twice. After 48 h of contact at 37° C. the media were replaced by XTT reagent. The plates were then placed in an incubator at 37° C. and the absorption was read after 6 hours. Controls with neither peptide nor protein were made on the same plate.

Figure 11:
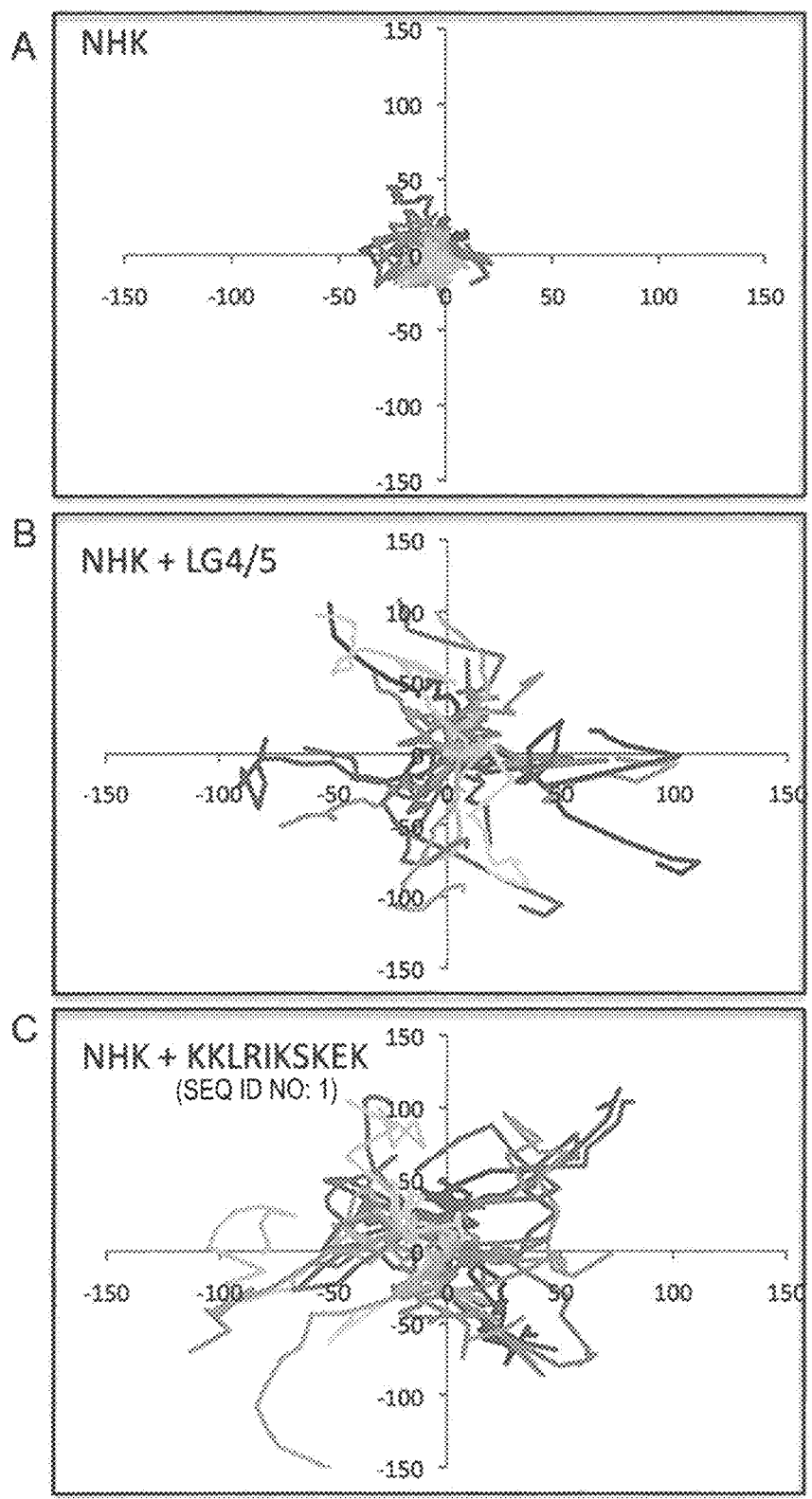

FIG. 11: Effect of the peptide KKLRIKSKEK (SEQ ID NO: 1) on the migration of NHKs by real-time videomicroscopy on living cells.

NHKs were seeded into 24-well plates at 20,000 cells per well in the absence (A) or presence of the LG4/5 fragment (10 μg/ml, B) or the peptide KKLRIKSKEK (SEQ ID NO: 1) (10 μg/ml, C) in KGM culture medium. The behaviour of the cells was then immediately recorded by real-time videomicroscopy (time-lapse) for 5 hours with an image being recorded every 10 minutes. The diagrams illustrate the behaviour of 20 cells taken at random in a given field. To facilitate data analysis, the paths were oriented from x(0), y.(0). The distances covered are shown in micrometers on the axes of graph.

Figure 12:
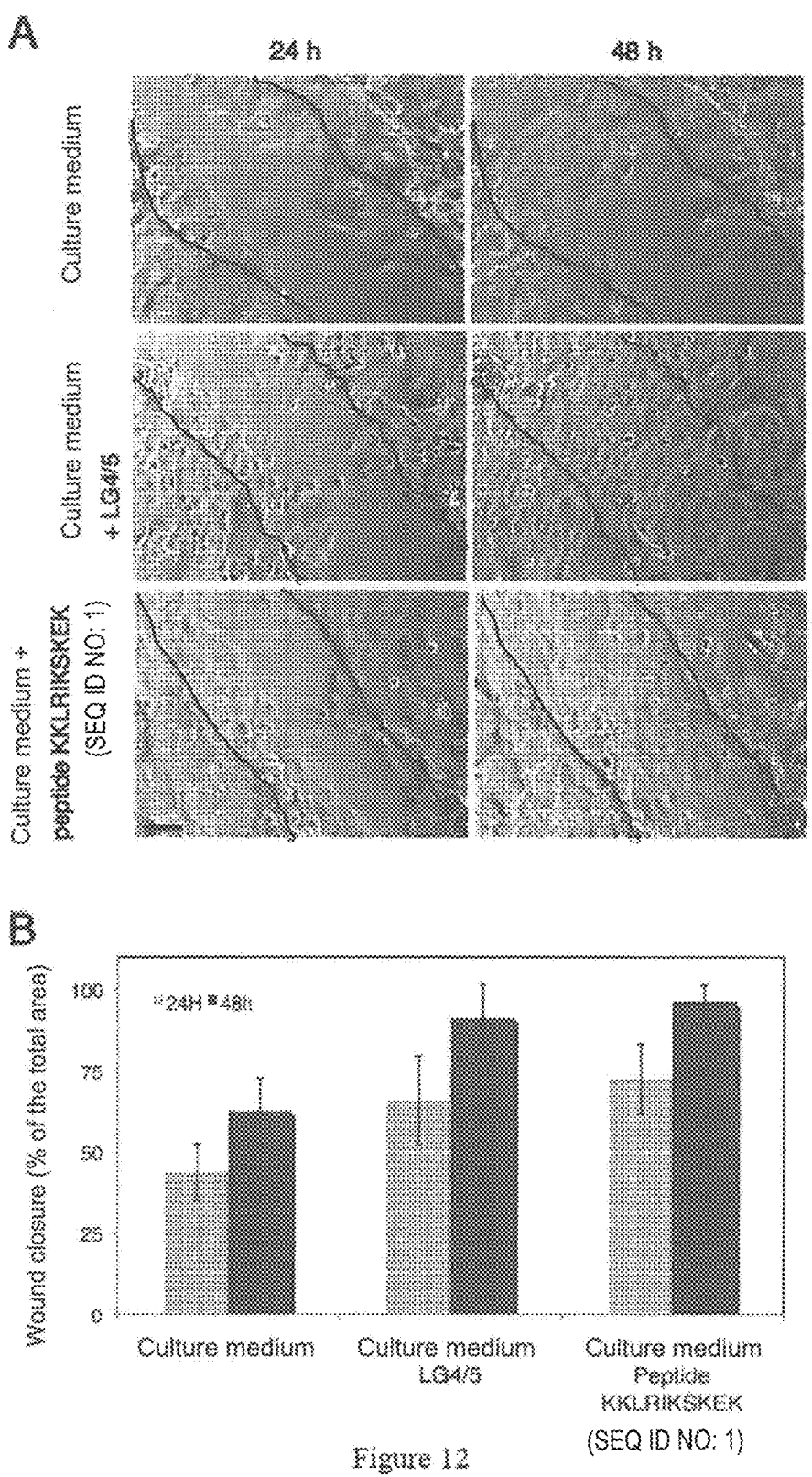

FIG. 12: Effect of the peptide KKLRIKSKEK (SEQ ID NO: 1) on NHK wound closure.

NHKs were seeded in 24-well plates and grown until confluence. The medium was removed and a wound was made in the cell layer using a pipette tip. After rinsing with PBS, the areas were incubated with KBM-2 culture medium at 37° C. in the absence or presence of LG4/5 protein (10 μg/ml) or the peptide KKLRIKSKEK (SEQ ID NO: 1) (20 μg/ml). The behaviour of cells around the wound was then immediately followed by time-lapse videomicroscopy with an image recorded every hour for 48 hours in a moist chamber containing 5% CO2. (A) Images recorded at the beginning of the experiment, at 24 h and 48 h show the total area of the wound covered by cells during the experiment and under each condition (the black lines represent the edges of the wound at the start of recording). Bar, 100 μM. (B) The wounded areas (without cells) were measured at the start, at 24 h (grey bars) and 48 h (black bars) using the Adobe Photoshop CS3

Extended program (version 10.0) in the different conditions. The rate of closure of each wound was expressed as a percentage of the initial wound. Each condition was performed in triplicate (3 wells per condition).

FIG. 13: Analysis of the effect of the peptide KKLRIK-SKEK (SEQ ID NO: 1) on cell adhesion to different extracellular matrix proteins.

(A) Study of the effect of the peptide in soluble form on the adhesion of HT1080 cells. With the help of dose-response adhesion experiments, a fixed quantity of collagen I (0.02° µg/well), collagen IV (0.5 µg/well), fibronectin (0.1 µg/well), laminin 111 (0.1 µg/well) and laminin 332 (0.2 µg/well) inducing average adhesion were chosen for this experiment and immobilised in 96-well plates. 6·10⁴ HT1080 cells were placed in each well in the presence (black bars) or absence (grey bars) of the peptide KKLRIKSKEK (SEQ ID NO: 1) (50 µg/ml). The plates were incubated at 37° C. for 1 hour and after washing, the adherent cells were fixed. Cell adhesion was measured as described in the methodology section. (B) Study of the effect of the immobilised peptide on HT1080 cell adhesion to matrix proteins. Matrix proteins, collagen I (0.02 µg), collagen IV (0.5 µg) fibronectin (0.1 µg), laminin 111 (0.1 µg) and laminin 332 (0.2 µg) were immobilised alone (grey bars) or co-immobilised with the peptide KKLRIK-SKEK (SEQ ID NO: 1) (2.5 µg, black bars) on 96-well plates. 6·10⁴ HT1080 cells were put in each well and the plates were incubated at 37° C. for 1 hour. After washing, the adherent cells were fixed and cell adhesion was measured as described in the methodology section.

Figure 14:
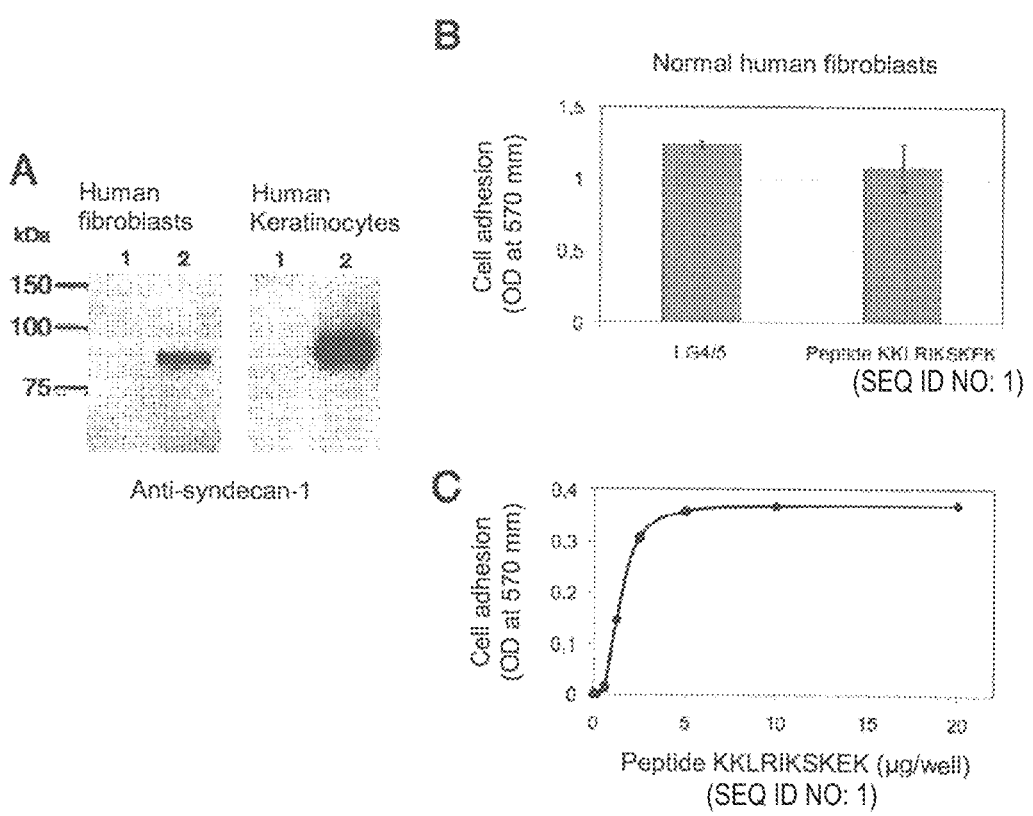

FIG. 14: Syndecan-1 in dermal fibroblasts interacts with the peptide KKLRIKSKEK (SEQ ID NO: 1).

(A) Showing the binding of syndecan-1 to the peptide KKLRIKSKEK (SEQ ID NO: 1). A lysate of normal human fibroblasts and a lysate of normal human keratinocytes were prepared as described in the Materials and Methods section and 2 mg of each lysate were incubated with neutravidin beads not coated (lines 1) or coated with the biotinylated peptide KKLRIKSKEK (SEQ ID NO: 1) (lines 2). A positive control was performed with the keratinocyte lysate to compare the size and quantity of syndecan-1 in the 2 cell types. After washing, the material bound to the beads was digested with a mixture of heparitinase I and chondroitinase ABC to release the protein part of the syndecan-1 from the glycosaminoglycans. The samples were then analysed by SDS PAGE electrophoresis in an 8% acrylamide gel under non-reducing conditions and by immunoblotting with polyclonal anti-syndecan antibody H174. The position of molecular weight markers is shown on the left. (B, C) Cell adhesion of normal human fibroblasts to the peptide KKLRIKSKEK (SEQ ID NO: 1) and to the LG4/5 protein. In one case (B), 5 µg of peptide KKLRIKSKEK (SEQ ID NO: 1) and 1 µg of protein LG4/5 were immobilised on a 96-well plate and in the other (C), the peptide KKLRIKSKEK (SEQ ID NO: 1) was immobilised at the concentrations indicated in the abscissa. 6·10⁴ dermal fibroblasts were put into each well and the plates were incubated at 37° C. for 1 hour. After washing, the adherent cells were fixed and cell adhesion was measured as described in the methodology section.

Figure 15:
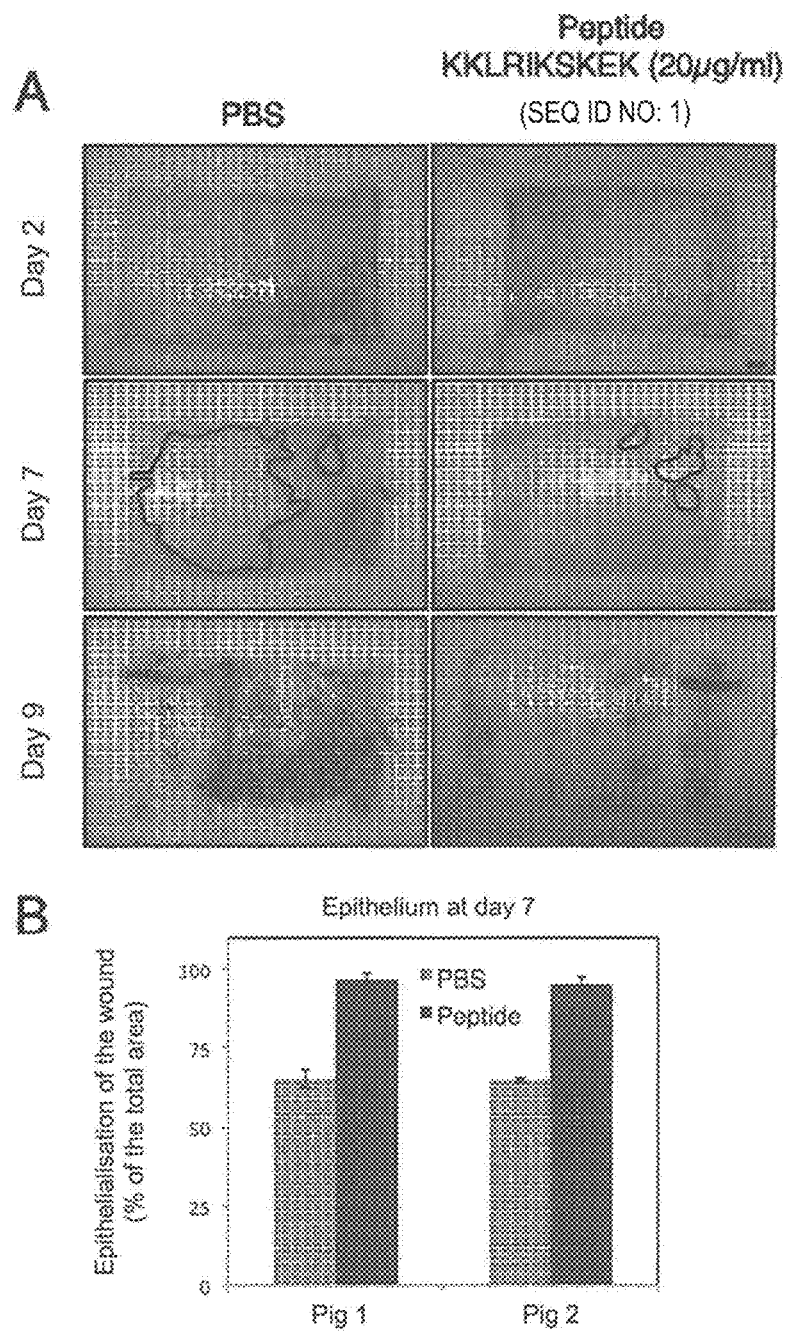

FIG. 15: Efficacy of the peptide KKLRIKSKEK (SEQ ID NO: 1) in epithelialisation of superficial skin wounds in an experimental model in the pig.

(A) Superficial wounds 0.9 mm deep were made on the backs of two pigs and were treated with PBS (control) or a solution of 20 µg/ml (pig 1) or 50 µg/ml (pig 2) of the peptide KKLRIKSKEK (SEQ ID NO: 1). Macroscopic assessment of the epithelialisation of the wounds showed a difference in cover between the two conditions on day 7. On the photographs, non-epithelialised areas have been surrounded by a black line. Macroscopic observation on day 11 showed better skin recovery in the presence of the peptide. (B) The re-epithelialised area of each wound photographed on day 7 was assessed using the Adobe Photoshop CS3 Extended program and the rate of epithelialisation was expressed as a percentage of the initial wound. These results are the mean of results obtained after treating four different wounds for each peptide concentration (2 control wounds per condition).

EXAMPLES OF EMBODIMENTS

1) Peptide Production Process

Peptide synthesis was performed on a Milligen 9050 synthesiser using Fmoc-Opfp/Hobt chemistry. The peptide was then detached from the resin and deprotected using a TFA solution containing scavengers (phenol, water, ethanedithiol and thioanisole). The peptide was then analysed and purified on a Vydac C18 5 mm column, of 4.6 or 10 mm diameter and 250 mm length and characterised by electrospray mass spectrometry on a SCIEX API 165. The biotinylated peptides were produced by Eurogentec (Eurogentec, Angers, France).

2) Information on the Peptide of Interest: KKLRIKSKEK (SEQ ID NO: 1)

Number of amino acids: 10
Molecular weight: 1257.5
Theoretical isoelectric point: 10.58
Amino Acid Composition:

| | | |
|---|---|---|
| Arg (R) | 1 | 10.0% |
| Glu (E) | 1 | 10.0% |
| Ile (I) | 1 | 10.0% |
| Leu (L) | 1 | 10.0% |
| Lys (K) | 5 | 50.0% |
| Ser (S) | 1 | 10.0% |

Total number of negatively charged residues (Asp+Glu): 1
Total number of positively charged residues (Arg+Lys): 6
Theoretical isoelectric points of peptide analogues between 10 and 12:

| | | | |
|---|---|---|---|
| A2: | KALRIKSKEK | (SEQ ID NO: 2): | 10.46 |
| A3: | KKARIKSKEK | (SEQ ID NO: 3): | 10.58 |
| A5: | KKLRAKSKEK | (SEQ ID NO: 4): | 10.58 |
| A6: | KKLRIASKEK | (SEQ ID NO: 5): | 10.46 |
| A8: | KKLRIKSAEK | (SEQ ID NO: 6): | 10.46 |
| A9: | KKLRIKSKAK | (SEQ ID NO: 7): | 11.39 |
| A10: | KKLRIKSKEA | (SEQ ID NO: 8): | 10.46 |
| M2: | KKLRLRSKER | (SEQ ID NO: 9): | 11.73 |
| M4: | KKLRHKSKEK | (SEQ ID NO: 10): | 10.58 |
| M5: | KKLRTKSKEK | (SEQ ID NO: 11): | 10.58 |
| M6: | KKLRKKSKEK | (SEQ ID NO: 12): | 10.68 |
| M7: | KKLRSKSKEK | (SEQ ID NO: 13): | 10.58 |
| M8: | KKLRIKLKEK | (SEQ ID NO: 14): | 10.58 |

-continued

| M9: | KKLRIKQKEK (SEQ ID NO: 15): | 10.58 |
| --- | --- | --- |
| U1: | KKLRIQSKEK (SEQ ID NO: 16): | 10.46 |
| U2: | KKLRIKSQEK (SEQ ID NO: 17): | 10.46 |
| U3: | KKLRIKSKEQ (SEQ ID NO: 18): | 10.46 |

3) The Cells Used for the Study

A—the Strains

The cells used were derived from strains expressing a large amount of syndecan-1 on their surface (Okamoto et al., 2003). These were cells of the strain HT1080 (fibrosarcoma, Human), American Type Culture Collection CCL-121.

These cells were maintained in culture in DMEM medium supplemented with 10% foetal calf serum and 2 mM glutamine and were cultured at 37° C. in a CO2 incubator (5% CO2, 95% air and 98% humidity).

B—the Primary Keratinocytes

Freshly isolated normal human keratinocytes were used. The human keratinocytes were obtained from foreskin biopsies (surgical waste, Pavillon T bis, Edouard Herriot Hospital). The culture medium used was the medium defined for culturing KGM-2 keratinocytes (containing: bovine pituitary extract 35 mg, hEGF 10 ng/ml, insulin 5 µg/ml, hydrocortisone 0.5 µg/ml, transferrin 0.1%, adrenaline 0.1%) made by Clonetics and marketed by Lonza (Belgium) containing 0.15 mM CaCl2, pH 7.2 to 7.4.

The keratinocytes were obtained using the technique described by Boyce and Ham (Cultivation, frozen storage, and clonal growth of normal human epidermal keratinocytes in serum-free media, Tiss Cult. Meth. 1985, 9:83-93). After being rinsed in PBS buffer containing antibiotics, the pieces of skin were separated from the fatty tissue below the dermis using sterile instruments. The skin was then cut into 3 mm$^2$ pieces, which were placed in a sterile solution of 0.25% trypsin in PBS for 16 hours at 4° C. The separation of the dermis from the epidermis was carried out using fine forceps in a Petri dish containing culture medium, in order to stop the enzyme action of trypsin. The fragments of epidermis were aspirated and expelled several times with a pipette to detach the free basal cells. The resulting cell suspension was centrifuged for 5 min at 1000 rpm and the pellet thus obtained was suspended in a known volume of KBM-2 to count the living cells using an exclusion dye: trypan blue. $3 \cdot 10^4$ living cells were seeded per cm$^2$ onto 25 cm$^2$ tissue culture dishes (Corning, Polylabo, France). The keratinocytes were cultured at 37° C. in a CO2 incubator (5% CO2, 95% air and 98% humidity). The medium was changed every two days. Subculturing occurred when the cells reached sub-confluence. The cell layer was then rinsed with PBS and covered with a trypsin-EDTA solution (0.05-0.02%). After a short incubation at 37° C., the cells were detached from the plastic support. The cells were then seeded into 75 cm$^2$ culture dishes. Cells were frozen (3 to 5 million per ampoule) in the culture medium used in the presence of 10% dimethyl sulphoxide (DMSO) and 20% calf serum in a volume of 1 ml.

C—the Primary Fibroblasts

Freshly isolated normal human fibroblasts were used. They were obtained from the foreskin biopsies used for obtaining the keratinocytes. The culture medium used was DMEM supplemented with 10% foetal calf serum and 2 mM glutamine. When the dermis had been separated from the epidermis, the fragments of dermis were placed for several days in petri dishes in the presence of DMEM supplemented with 10% foetal calf serum and 2 mM glutamine at 37° C. in a CO2 incubator (5% CO2, 95% air and 98% humidity). The medium was changed every two days. When the fibroblasts had been removed from the dermal explants and had colonised the petri dish, they were loosened from the dish with trypsin and amplified by conventional cell culture techniques.

4) Quantitative Analysis of the Cell Adhesion Properties of the Peptide of Interest by a Colorimetric Test —Preparation of the Adhesion Substrates Peptides, purified LG4/5 protein (Belin and Rousselle, 2007) and purified LN332 (Rousselle et al., 1991) were used in the cell adhesion experiments. A range of 7 decreasing concentrations was produced by successive dilution in PBS (phosphate buffered saline, $KH_2PO_4$ 1.54 mM; $Na_2HPO_4$ 1.42 mM; NaCl 131 mM) or immobilisation buffer $Na_2CO_3$ 20 mM pH 9, from a 1 mg/ml starting solution. These solutions were immediately distributed onto 96-well culture plates (Greiner, Dutscher, Brumath, France) at 100 µl per well. The other matrix proteins, bovine collagen I (Symatèse Biomatériaux), human collagen IV, fibronectin and human laminin 1 (BD Biosciences, Le Pont de Claix, France) were prepared in PBS and distributed onto 96-well plates (Corning, Amsterdam, Netherlands). The plates were then placed at +4° C. for 16 to 18 hours. The solutions were then removed by inverting the plates and each well was saturated with a solution of PBS-BSA 1% (bovine serum albumin) Three additional wells without substrate underwent the same treatment and served as control.

The experiments comparing the adhesion induced by the peptides KKLRIKSKEK (SEQ ID NO: 1) and NSFMALYL-SKGR (SEQ ID NO: 21) were performed using Microlon 96-well plates (Greiner, Dutscher) on which the two peptides had been immobilised with the same efficacy. The amount of peptide immobilised was determined with bicinchoninic acid (BCA Protein Assay, Perbio Science, Brebière, France).

—Cell Adhesion Test

The cells were detached from the culture dishes with a solution of PBS/EDTA 10 mM and were then suspended in DMEM without additives for the cell strains and KBM-2 without additives for the human keratinocytes. The number of cells seeded per well is shown on the graphs ($5 \cdot 10^4$ to $10^5$ cells per well).

—Evaluation of the Cell Adhesion Test

After seeding the cells, the multiwell plates were placed in an incubator at 37° C. in an atmosphere of 5% CO2. After incubation for 30 to 60 minutes, the cells were observed under a phase contrast microscope to check that the test had taken place correctly. The adhesion medium was then removed and each well was washed with sterile PBS solution to remove cells which had not adhered. The remaining cells, adhering to the substrate, were then fixed for 15 minutes with a solution of 1% glutaraldehyde in PBS. The glutaraldehyde solution was removed and the cells were then stained for 30 minutes with a solution of crystal violet diluted to 1% in distilled water. After extensive rinsing in water, the cells were permeabilised for 15 minutes with a solution of 0.02% triton, to dissolve the crystal violet. The absorption reading was made at 570 nm using an ELISA plate reader (MR500, Dynatech, Guernsey, Channel Islands). Each experimental point was performed in triplicate. The blank value is the mean absorption of 3 control wells (BSA). This was subtracted from each of the optical density values obtained for the experimental points. The mean of the three absorption values was then calculated for each set of three points.

The results were shown as a graph with, as ordinate, the absorption values and as the abscissa, the different substrate concentrations. The adherent cells were photographed using phase contrast microscopy.

5) Tests of Inhibition of Cell Adhesion by Competition 96-well plates were coated with the amounts indicated of peptide KKLRIKSKEK (SEQ ID NO: 1) or laminin 332 by adsorption at +4° C. for 16 to 18 hours. As before, the wells were saturated with a solution of 1% PBS-BSA for one hour. The HT1080 cells were detached from the culture dishes and were then suspended in serum-free DMEM. After counting the cells, the whole LG4/5 protein or the peptide was added to the cell suspension 30 minutes before the adhesion test. A control without competitor was systematically performed and was considered as 100% adhesion. In the case of inhibition by anti-LG4/5 antibodies, the latter were applied to the immobilised proteins for one hour after the saturation with 1% PBS-BSA.

6) Cell Viability Test

The effect of the peptide on the cell viability of the normal human keratinocytes was analysed using a colorimetric assay (XTT Cell Proliferation Kit, Roche Diagnostics, Meylan, France). A control with the LG4/5 protein was carried out in parallel. The chemical reaction of the test is based on the production of NADPH in living cells reducing yellow tetrazolium XTT salts to orange formazan salts. Absorption at 490 nm is measured using an ELISA plate reader. The cells were seeded in 96-well plates at 10,000 cells per well (6 wells/condition) in KBM-2 culture medium. After 24 hours of culture at 37° C. with 5% CO2, the culture media were removed and replaced with serum-free medium containing the quantities of peptide or protein shown on the graphs and the assay reagent. The plates were then put into an incubator at 37° C. and absorption readings taken at 1 h, 2 h, 3 h, 4 h and 5 h. Controls with neither peptide nor protein were made on the same plate. The results are shown as the percentage viability of the cells in the presence of the peptide or protein, relative to the controls with neither peptide nor protein. In this case, cell viability was calculated from the formula:

% viability=(Abs. cells with peptide/Abs. control cells)×100.

7) Affinity Chromatography Assays and Syndecan-1 Detection

To identify the nature of the cell receptor binding to the peptide KKLRIKSKEK (SEQ ID NO: 1), affinity chromatography or 'pull-down' assays were performed by incubating beads coated with peptides with cell lysates. Lysates of primary keratinocytes or fibroblasts were made using a lysis buffer of 1% triton X-100 in PBS, pH 7.5, containing N-ethylmaleimide and phenylmethylsulphonylfluoride 50 mM. The wild type peptide KKLRIKSKEK (SEQ ID NO: 1) and the mutated peptides were bound to biotin at their amino-terminal ends and 100 µg of each biotinylated peptide were attached to agarose-neutravidin beads (Perbio Science, Bezons, France) by incubation for 16 hours at +4° C. The beads were then incubated with 2 mg of cell lysate for 2 hours at +4° C. After washing 3 times with the lysis buffer, the beads were transferred into a digestion buffer (20 mM sodium acetate, 5 mM CaCl2, pH 7.0) containing 8 mU/ml heparitinase I and 50 mU/ml of chondroitinase ABC (Seikagaku America, Coger, Paris, France) for 2 hours at 25° C. This treatment strips the protein part of syndecan-1 of glycosaminoglycans, making it easier to analyse by immunoblotting. The samples were then analysed by SDS PAGE electrophoresis in an 8% acrylamide gel under non-reducing conditions and by immunoblotting with polyclonal anti-syndecan antibody H174 (Santa Cruz Biotechnology, Le Perray en Yvelines, France).

8) Real Time Videomicroscopy on Living Cells (Time Lapse)

Videomicroscopy experiments were performed with a Zeiss Axiovert 100M microscope fitted with a CCD camera (1 image every 10 minutes or every hour). In the experiments of FIG. 11, we analysed the movements of 100 cells using Metaview software (Roper Scientific, Princeton Instruments, Evry, France).

9) Healing In Vivo

Skin wounds 12 cm long, 8 cm wide and 0.9 mm deep were made using a dermatome on the backs of two female pigs that were approximately 4 months old (2 control and 4 treated wounds per pig, on either side of the vertebral column). Two concentrations of peptide, 20 µg/ml (pig 1) and 50 µg/ml (pig 2) and a PBS solution (controls) were applied to the wounds on the first day and at each dressing change (D1, D2, D4, D7 and D11). Following clinical analysis, photographs and skin biopsies were taken. The epithelialised area was evaluated from photographs from day 7 using the Adobe Photoshop CS3 Extended program (version 10.0). The experiment was conducted at the Claude Bourgelat Institute Veterinary Campus (VetAgro Sup), Lyon, and the protocol was approved by the ethics committee of the VetAgro Sup veterinary campus.

Results:

a/ Study of the Adhesion of Normal Human Keratinocytes and HT1080 Cells to the LG4/5 Fragment and to the Peptide KKLRIKSKEK (SEQ ID NO: 1)

As shown in FIG. 3, the peptide KKLRIKSKEK (SEQ ID NO: 1) induces cell adhesion of HT1080 cells and normal human keratinocytes in a dose dependent manner. A control adhesion experiment was performed with the same cells on the purified whole LG4/5 fragment to show syndecan-1 dependent adhesion and to compare the cell morphology obtained between the whole LG4/5 fragment and the syndecan-1 peptide interaction sequence. The cells are firmly anchored to the peptide since, like the whole LG4/5 fragment, they resisted the various washes before fixing. Maximum cell adhesion was obtained when a mean quantity of 10 micrograms of peptide was placed in the wells for immobilisation. The adhesion profile of the two cell types, HT1080 and NHK, is identical on the peptide of interest. This experiment is qualitative and was performed in order to analyse the behaviour of the cells in contact with the peptide. The concentrations inducing adhesion are thus indicative as (1) they do not reflect the actual amount of peptide immobilised in the wells and (2) they depend on the quantity of cells in each well. These observations indicate that the quantities announced have been over-assessed and that smaller quantities could induce syndecan-1 dependent cell adhesion. Indeed, a relatively small number of cells was used deliberately in this experiment in order to show the dose-response effect and to analyse the morphology of individual cells. Too confluent a layer would have hindered this observation. The photographs obtained by phase contrast microscopy showed that the morphology of the HT1080 cells and keratinocytes adhering to the peptide KKLRIKSKEK (SEQ ID NO: 1) was the same as that of these cells adhering to the whole LG4/5 fragment. This indicates that the peptide KKLRIKSKEK (SEQ ID NO: 1) is able to induce the adhesion properties carried by the whole LG4/5 fragment. As extensively described in the applicant's publications, adhesion to LG4/5 induces the cell to spread out with protruding cytoplasmic prolongations in the form of filopodia (Décline et al., 2003, Okamoto et al., 2003, Bachy et al., 2008, Sulka et al., 2009). These structures associated with the actin cytoskeleton are involved in the process of cell migration.

To confirm that the peptide KKLRIKSKEK (SEQ ID NO: 1) corresponds to the sequence responsible for cell adhesion on the LG4/5 fragment, competitive experiments were performed by preincubating the cells with the peptide KKLRIK-SKEK (SEQ ID NO: 1) before making them adhere to the LG4/5 fragment (FIG. 4). In this experiment, cell adhesion was also tested on LN332 to ensure the specificity of the effect of the peptide on the LG4/5 protein and not on other matrix proteins. A specific positive control inhibiting adhesion to LG4/5 was performed with a polyclonal anti-LG4/5 antibody we had characterised as blocking the LG4/5 function. The whole LG4/5 protein was also used as a positive control in this experiment. Thus, the HT1080 cells were either used as they were, or were pre-incubated with the whole LG4/5 protein or with the peptide. They were then deposited on the LG4/5 and LN332 substrates for the adhesion experiment. As expected, our anti-LG4/5 antibody inhibited the adhesion to the LG4/5 fragment without altering adhesion to the LN332. By binding to the syndecan-1 of the cells, the LG4/5 fragment added as a solution also blocked adhesion to the immobilised LG4/5 fragment without affecting adhesion to LN332. The peptide KKLRIKSKEK (SEQ ID NO: 1) added as a solution, also completely blocked cell adhesion to the LG4/5 fragment and did not affect adhesion to LN332. This result shows that the peptide was able alone to bind to the receptor involved in adhesion to the LG4/5 fragment. The fact that it did not inhibit adhesion to LN332 confirms the specificity of its activity on the LG4/5 fragment. These results show that the KKLRIK-SKEK sequence (SEQ ID NO: 1) is the sequence responsible for syndecan-1 dependent adhesion to the LG4/5 fragment. They also show that the LG4/5 fragment and the peptide KKLRIKSKEK (SEQ ID NO: 1) added in soluble form, both have the ability to interact with the cells and bind to the syndecan-1 receptor. This indicates that these proteins could also activate syndecan-1 dependent signalling pathways when added in a soluble form.

b/ Demonstration of Specific Binding of Syndecan-1 to the Peptide KKLRIKSKEK (SEQ ID NO: 1) by Affinity Chromatography To demonstrate that the peptide KKLRIKSKEK (SEQ ID NO: 1) is the site of interaction of syndecan-1 on the LG4/5 fragment, affinity chromatography experiments were performed by fixing the KKLRIKSKEK peptide (SEQ ID NO: 1) combined with biotin on streptavidin beads. The peptide thus exposed on the surface of the beads served as a molecular hook to trap its receptor in an extract of normal human keratinocytes. In this experiment, the other two sequences identified in the LG4/5 fragment as being involved in heparin binding (PSGKPKSLP (SEQ ID NO: 19) and TSVTPKQSL (SEQ ID NO: 20), Vives et al., 2003) were also biotinylated and tested. Primary keratinocyte homogenates were prepared and the beads coated with the different peptides were incubated with equivalent quantities of these lysates (FIG. 5A). The proteins fixed to the beads were then analysed by SDS-PAGE electrophoresis followed by immunodetection to assess their syndecan-1 content. As shown in FIG. 5A, only the protein extract fixed to the beads coated with the peptide KKLRIKSKEK (SEQ ID NO: 1) (line 2) has a protein recognised by the anti-syndecan-1 antibody. The beads not coated with peptide (negative control, line 1) and the beads coated with the other two peptides (lines 3 and 4) did not retain the syndecan-1. To confirm that the protein associated with the peptide KKLRIKSKEK (SEQ ID NO: 1) was indeed syndecan-1, the experiment was repeated using the whole LG4/5 fragment as positive control (FIG. 5B). In this case, the protein purified by the peptide KKLRIKSKEK (SEQ ID NO: 1) (line 3) is indeed syndecan-1, since it corresponds to the protein purified by the whole LG4/5 fragment (line 2). The beads not coated with peptide showed no nonspecific binding (line 1). These results show that syndecan-1 is a specific receptor for peptide KKLRIKSKEK (SEQ ID NO: 1) in a way comparable to the whole LG4/5 fragment.

c/ Adhesion of HT1080 Cells to the Peptides KKLRIKSKEK (SEQ ID NO: 1) and NSFMALYLSKGR (SEQ ID NO: 21) (Described in JP2006063033).

By an approach based on the production of peptides sequentially covering the entire sequence of the LG4/5 modules, another sequence has been identified as inducing cell adhesion (Utan et al., 2001 and JP2006063033) via other receptors such as syndecan 2 or 4. This sequence NSFMA-LYLSKGR (SEQ ID NO: 21) (from residue 1412 to residue 1423 of the sequence of the alpha3 chain) is located in the LG4 module. To compare the capacity of the peptide KKL-RIKSKEK (SEQ ID NO: 1) to induce cell adhesion with this peptide sequence, a comparative adhesion test was performed with HT1080 cells which express syndecan-1 (FIG. 6). The two peptides were immobilised on 96-well plates and the amount of peptide adsorbed was quantified to ensure equivalent quantities of peptide in both cases. A range of peptide actually immobilised was produced, with between 2 µg and 0.07 µg per well. After being detached from the culture dishes under conditions conserving the syndecans, the HT1080 cells were deposited in the wells containing the two peptides and remained in contact for one hour in the absence of serum (FIG. 6A). Quantitative analysis of cell adhesion showed that the peptide KKLRIKSKEK (SEQ ID NO: 1) is more effective than the peptide NSFMALYLSKGR (SEQ ID NO: 21) since (1) cell adhesion was induced for a lower quantity of immobilised peptide (about 0.025 µg) and (2) the maximum cell adhesion reached at the plateau was significantly higher (about 200%). Analysis of cell morphology also showed that, while the cells adhering to KKLRIKSKEK (SEQ ID NO: 1) exhibit the morphology typical of syndecan-1 dependent adhesion to fragment LG4/5 (see FIG. 3), adhesion of cells to the peptide NSFMALYLSKGR (SEQ ID NO: 21) was not accompanied by the same cell spreading since no cytoplasmic prolongations were noted (FIG. 6B). Adhesion to this peptide has been described as involving syndecans-2 and -4 (Utan et al., 2001). This suggests that this peptide could be involved in different cell processes from those we are describing for the peptide KKLRIKSKEK (SEQ NO: ID 1).

d/ Mutations

In order to characterise the activity of the peptide KKL-RIKSKEK (SEQ ID NO: 1), the importance was evaluated of different amino acids in the interaction with the syndecan-1 by performing a number of substitutions of these amino acids. This work also aimed to identify the residues essential for activity of the peptide. In the first instance, in order to cause the least structural alterations of the peptide, each amino acid of the sequence KKLRIKSKEK (SEQ ID NO: 1) was successively substituted by a neutral amino acid, alanine (A) (FIG. 7). The syndecan-1 recruitment experiments with this series of mutated peptides showed that the individual substitution of three residues is sufficient to inhibit interaction with syndecan-1. These residues are amino acid 1: a lysine (K), amino acid 4: an arginine (R) and amino acid 7: a serine (S). There are five lysine residues in the peptide sequence KKL-RIKSKEK (SEQ ID NO: 1), and only mutation of the first caused complete loss of the interaction activity of the peptide. This indicates that the activity of each of the other lysine residues was compensated during interaction with syndecan- 1. To characterise the role of lysine residues in the peptide sequence more precisely, the charge of each of these residues was modified, and the impact of this change on binding to syndecan-1 was analysed. To do this, these amino acids were replaced by a glutamine (Q), a neutral amino acid at physiological pH (FIG. 8). These mutations were either point (a single amino acid substituted) or grouped (2 or 3 simultaneous substitutions).

e/ Homologous Sequences

Homologous sequences to the KKLRIKSKEK sequence (SEQ ID NO: 1) were sought in the extracellular matrix proteins to identify a potential homologous sequence with the properties for binding to syndecan-1 and to be sure of the specificity of the activity of this sequence. The 4 extracellular matrix proteins identified as having a sequence homologous to the KKLRIKSKEK sequence (SEQ ID NO: 1) of the human laminin alpha3 chain are the murine laminin alpha3 chain (M2), the human (M1) and murine (M1) laminin alpha4 chains and the transmembrane protein ADAM 20 (M3) (FIG. 9A). All these sequences were tested for their ability to bind syndecan-1 and only the sequences of human and murine laminin alpha3 and alpha4 proved capable of binding syndecan-1 whereas the sequence of the protein ADAM 20 was inactive (FIG. 9C).). All these results show that the syndecan-1 binding sequence in the human laminin alpha3 chain is conserved in the mouse. Moreover, a homologous sequence is present in the laminin alpha4 chain. The fact that the sequence present in the ADAM 20 protein does not bind syndecan-1 emphasizes the specificity and uniqueness of the sequence present in the laminins. To support the possibility of substituting some residues, homologous sequences were sought on fragments of the peptide sequence and the sequences identified were replaced in the context of the whole peptide (FIG. 9B). In particular, substitutions of amino acid 5 (isoleucine, M4 to M7) and amino acid 7 (serine, M8 and M9) were identified. It can be seen in FIG. 9C that none of these mutations resulted in inhibiting the interaction.

f/ Cell Viability

Finally, to ensure that the peptide had no toxic effect on the keratinocytes, cell viability was tested using a range of peptide concentrations from 100 to 1 µg/ml. A control with the LG4/5 protein was carried out in parallel (FIG. 10). The keratinocytes were seeded in 96-well plates at $10^4$ cells per well. After 24 hours, the culture media were removed and replaced with KBM-2 medium containing the quantities of peptide (pink curve) or LG4/5 protein (blue curve) shown on the graphs. After two days at 37° C., this step was repeated twice and the living cells were quantified using the XTT reagent test. The results, presented as the percentage of viable cells in the presence of the peptide or LG4/5 protein compared with controls, show that neither peptide KKLRIKSKEK (SEQ ID NO: 1) nor protein LG4/5 has any long-term cytotoxic effect on epidermal keratinocytes.

g/ Induction of Cell Migration

The effect of the addition of the whole LG4/5 fragment or the KKLRIKSKEK sequence (SEQ ID NO: 1) in soluble form to the culture medium of normal human keratinocytes was analysed by real time videomicroscopy on living cells. Initially, the observation of keratinocytes for 5 hours highlighted significant differences depending whether the peptide was present or absent. The normal keratinocytes maintained in standard culture medium made circular movements of small amplitude, the total distance of which never exceeded 40 µm (FIG. 11A). Adding the LG4/5 protein or the peptide KKLRIKSKEK (SEQ ID NO: 1) to the culture medium induced a drastic change in behaviour (FIGS. 11B and C). In both cases, the circular movements of the keratinocytes were replaced by random linear displacement with the distance (from the origin) reaching as much as 150 µm. These results show that the LG4/5 fragment induces cell migration when it binds to cells. The peptide KKLRIKSKEK (SEQ ID NO: 1) is capable of reproducing the activity of the LG4/5 fragment. While adhesion to the LG4/5 fragment plays an important role in cell migration induced by pre-LN332, this same LG4/5 fragment (or its minimum sequence KKLRIKSKEK (SEQ ID NO: 1)) is capable of inducing cell migration alone.

The effect of the LG4/5 fragment and the peptide was also analysed on the closure of a wound made in the centre of a confluent keratinocyte layer (FIG. 12). As with the in vivo wounds, closure occurred in this model by the migration and proliferation of keratinocytes located at the edges of the wound. In the control conditions (culture medium only) the wound closed gradually and measurements showed that the cells had covered 43% of the area of the wound after 24 h and 62% after 48 h. When the LG4/5 protein was added to the culture medium, the cells covered 65% of the area at 24 h and 91% at 48 h, indicating that this domain of laminin 332 accelerates the process of wound closure. This effect was found or even amplified with the peptide KKLRIKSKEK (SEQ ID NO: 1) because wound closure was 72% at 24 h and 96% at 48 h (FIGS. 12A and B). The peptide has properties inducing skin healing.

The hypothesis that the peptide has properties inducing skin healing was verified by studying the efficacy of the peptide in epithelialisation of superficial skin wounds in an experimental model in pigs (FIG. 15). Pig skin tissue has similar characteristics to that of human skin. Application of the peptide on 0.9 mm deep injuries promoted closure of the wound (FIG. 15A). Indeed, in the controls (using PBS), the wound closed gradually and measurements showed that the epithelium had covered 65% of the injured area 7 days after the wound was made. When the wound was treated with the peptide (20 µg/ml or 50 µg/ml), the percentage of re-epithelialisation of the wound was almost complete on the seventh day as it had reached 96% of the surface. This experiment shows that the peptide accelerates the process of wound closure in vivo. After treatment with the peptide, macroscopic observation of the wounds after total closure (day 11, FIG. 15A) revealed uniform, healthy skin tissue with identical properties to the tissue surrounding the repaired area, whereas in the case of the control it still appeared fragile and bruised. These results indicate that repaired skin appears to be stronger and of better quality when it has been treated with the peptide.

h/ Effect of Peptide on the Adhesion of Cells to the Extracellular Matrix

In order to analyse the effect of the peptide KKLRIKSKEK (SEQ ID NO: 1) as regards the extracellular matrix of the skin, we performed experiments on adhesion to these matrix proteins in the presence of the peptide provided either in soluble form or co-immobilised with these proteins. The matrix proteins tested (collagen I, collagen IV, fibronectin, laminin 111 and laminin 332) are widely known to induce the adhesion of skin cells through receptors belonging to the integrin family. To analyse the effect of the peptide on the adhesion of cells to these matrix proteins, the peptide KKLRIKSKEK (SEQ ID NO: 1) was put into contact with HT1080 cells, previously dissociated using EDTA, before being deposited on the substrate matrices (FIG. 13A). Analysis of the adhesion obtained by the control cells (without the peptide, grey bars) and by cells treated with the peptide (black bars) to the various matrix proteins showed an increase in adhesion by 20 to 50% depending on the proteins. This effect was even more pronounced when the peptide was co-immobilised with these proteins (FIG. 13B), since a range of 20 to 150% of increase in adhesion was observed. All of these results indicate that the peptide KKLRIKSKEK (SEQ ID NO: 1) potentiates the adhesion of HT1080 cells to extracellular matrix proteins. The peptide KKLRIKSKEK (SEQ ID NO: 1) increases the affinity of the cells for the proteins of the extracellular matrix and thus allows better communication with the microenvironment.

i/ Study of the Adhesion of Normal Human Fibroblasts to the LG4/5 Fragment and to the Peptide KKLRIKSKEK (SEQ ID NO: 1)

To demonstrate that dermal fibroblasts express syndecan-1 and that it can interact with the peptide KKLRIKSKEK (SEQ ID NO: 1), a chromatography experiment on affinity to the peptide KKLRIKSKEK (SEQ ID NO: 1) was performed with a lysate of normal human fibroblasts (FIG. 14A). A control experiment was performed with primary keratinocytes. The proteins fixed to beads were then analysed by SDS-PAGE electrophoresis followed by immunodetection to assess their syndecan-1 content. As shown in FIG. 14A, syndecan-1 is expressed by the fibroblasts and binds to the peptide KKLRIKSKEK (SEQ ID NO: 1). Cell adhesion experiments show that human dermal fibroblasts adhere to the whole LG4/5 domain and to the peptide KKLRIKSKEK (SEQ ID NO: 1) (FIG. 14B). As shown in FIG. 14C, the KKLRIKSKEK peptide (SEQ ID NO: 1) induces adhesion of normal human fibroblasts in a dose dependent manner. Maximum cell adhesion was obtained when a mean quantity of 5 micrograms of peptide was placed in the wells for immobilisation. The morphology of the fibroblasts adhering to the peptide KKLRIKSKEK (SEQ ID NO: 1) and to the LG4/5 fragment was spread out, with cytoplasmic prolongations (data not shown). The peptide KKLRIKSKEK (SEQ ID NO: 1) interacts with dermal fibroblasts and is an adhesion substrate allowing them to anchor to their matrix microenvironment and to spread out, conditions which promote tissue repair and regeneration.

BIBLIOGRAPHY

Amano S, Scott I C, Takahara K, Koch M, Champliaud M F, Gerecke D R, Keene D R, Hudson D L, Nishiyama T, Lee S, Greenspan D S, and Burgeson R E. (2000) J. Biol. Chem. 275, 22728-22735.

Aumailley M, Gimond C, and Rousselle P. (1996) Integrin-mediated cellular interactions with laminins In "The laminins" Eds. P. Ekblom, R. Timpl, Harwood Academic Publishers, pp 127-158.

Aumailley M, and Rousselle P. (1999) Laminins of the dermo-epidermal junction. Matrix Biol., 18:19-28.

Bachy S, Letourneur F, and Rousselle P. (2008) Syndecan-1 interaction with the LG4/5 domain in laminin-332 is essential for keratinocyte migration. J Cell Physiol., 214:238-249.

Baker S E, Hopkinson S B, Fitchmun M, Andreason G L, Frasier F, Plopper G, Quaranta V, and Jones J C. (1996) J. Cell Sci. 109, 2509-2520.

Belin V, and Rousselle P. (2006) Production of a recombinantly expressed laminin fragment by HEK293-EBNA cells cultured in suspension in a dialysis-based bioreactor. Protein Expr. Purif. 48:43-48.

Bernfield M, Gotte M, Park P W, Reizes O, Fitzgerald M L, Lincecum J, and Zako M. (1999) Functions of cell surface heparan sulfate proteoglycans. Ann. Rev. Biochem. 68, 729-777.

Clark R A F. (1996). Wound repair: overview and general considerations. In: The molecular and cellular biology of wound repair. Clark R. A. F, Editor. Plenum Press/New York. 3-50.

Decline F, and Rousselle P. (2001). Keratinocyte migration requires alpha2beta1 integrin-mediated interaction with the laminin 5 gamma2 chain. J. Cell Sci. 114:811-823.

Decline F, Okamoto O, Mallein-Gerin F, Helbert B, Bernaud J, Rigal D, Rousselle P. (2003). Keratinocyte motility induced by TGF-beta1 is accompanied by dramatic changes in cellular interactions with laminin 5 Cell Motil. Cytoskeleton 54:64-80.

Elenius K, Vainio S, Laato M, Salmivirta M, Thesleff I and Jalkanen M. (1991). Induced expression of syndecan in healing wounds. J. Cell Biol. 114:585-595.

Frank D E and Carter W G. (2004). Laminin 5 deposition regulates keratinocyte polarization and persistent migration. J. Cell Sci. 117:1351-1363.

Gallo R, Kim C, Kokenyesi R, Adzick N S and Bernfield M. (1996) Syndecans-1 and -4 are induced during wound repair of neonatal but not fetal skin. J. Invest. Dermatol. 107:676-683.

Ghohestani R F, Li K, Rousselle P, and Uitto J. (2001) Molecular organization of the cutaneous basement membrane zone. Clin. Dermatol., 19:551-562.

Goldfinger L E, Hopkinson S B, deHart G W, Collawn S, Couchman J R, and Jones J C. (1999) The alpha3 laminin subunit, alpha6beta4 and alpha3beta1 integrin coordinately regulate wound healing in cultured epithelial cells and in the skin. J. Cell Sci. 112:2615-2629.

Goldfinger L E, Stack M S, and Jones J C. (1998) Processing of laminin-5 and its functional consequences: role of plasmin and tissue-type plasminogen activator. J. Cell Biol. 141: 255-265.

Hynes R O. (1992) Integrins: versatility, modulation, and signaling in cell adhesion. Cell 69:11-25.

Jaakkola P, Kontusaari S, Kauppi T, Maata A, and Jalkanen M. (1998) Wound reepithelialization activates a growth factor-responsive enhancer in migrating keratinocytes. FASEB J 12: 959-969.

Lampe P D, Nguyen B P, Gil S, Usui M, Olerud J, Takada Y, and Carter W G. (1998) Cellular interaction of integrin alpha3beta1 with laminin 5 promotes gap junctional communication. J. Cell Biol. 143, 1735-1747.

Larjava H, Salo T, Haaspasalmi K, Kramer R H, Heino J. (1993) Expression of integrins and basement membrane components by wound keratinocytes. J. Clin. Invest. 92:1425-1435.

Marinkovich M P, Lunstrum G P, and Burgeson R E. (1992) The anchoring filament protein kalinin is synthesized and secreted as a high molecular weight precursor. J. Biol. Chem. 267, 17900-17906.

Masuda R, Mochizuki M, Hozumi K, Takeda A, Uchinuma E, Yamashina S, Nomizu M, Kadoya Y. (2009) A novel cell-adhesive scaffold material for delivering keratinocytes reduces granulation tissue in dermal wounds. Wound Repair Regen. 17:127-135.

Nguyen B P, Ryan M C, Gil S G and Carter W G. (2000) Deposition of laminin 5 in epidermal wounds regulates integrin signaling and adhesion. Curr. Opin. Cell Biol. 12:554-562.

Niessen C M, Hogervorst F, Jaspars L H, de Melker A A, Delwel G O, Hulsman E H, Kuikman I and Sonnenberg A. (1994) The alpha 6 beta 4 integrin is a receptor for both laminin and kalinin. Exp Cell Res 211:360-367.

Okamoto O, Bachy S, Odenthal U, Bemaud J, Rigal D, Lortat-Jacob H, Smyth N and Rousselle P. (2003) Normal human keratinocytes bind to the alpha3LG4/5 domain of unprocessed laminin-5 through the receptor syndecan-1. J. Biol. Chem. 278:44168-44177.

Oksala O, Salo T, Tammi R, Hakkinen L, Jalkanen M, Inki P and Larjava H. (1995) Expression of proteoglycans and hyaluronan during wound healing. J. Histochem. Cytochem. 43:125-135.

Rousselle P, Aumailley M. (1994) Kalinin is more efficient than laminin in promoting adhesion of primary keratinocytes and some other epithelial cells and has a different requirement for integrin receptors. J. Cell Biol. 125: 205-214.

Rousselle P, Keene D R, Champliaud M F, Van der Rest M, and Burgeson R. E. (1997) Laminin 5 binds type VII collagen thru its NC1 domain. J. Cell Biol. 138:719-728.

Rousselle P, Lunstrum G P, Keene D R, and Burgeson R E. (1991) Kalinin: an epithelium-specific basement membrane adhesion molecule that is a component of anchoring filaments. J. Cell Biol. 114:567-576.

Ryan M C, Lee K, Miyashita Y, and Carter W G. (1999) Targeted disruption of the LAMA5 gene in mice reveals abnormalities in survival and late stage differentiation of epithelial cells. J. Cell Biol. 145:1309-1323.

Ryan M C, Tizard R, VanDevanter D R and Carter W G. (1994) Cloning of the LamA3 gene encoding the alpha 3 chain of the adhesive ligand epiligrin. Expression in wound repair. J. Biol. Chem. 269:22779-22787.

Sigle R O, Gil S G, Bhattacharya M, Ryan M C, Yang T M, Brown T A, Boutaud A, Miyashita Y, Olerud J, and Carter WG. 2004. Globular domains 4/5 of the laminin alpha3 chain mediate deposition of precursor laminin 5 J Cell Sci. 117:4481-4494.

Sonnenberg A, de Melker A A, Martinez de Velasco A M, Janssen H, Calafat J, and Niessen C M. (1993) Formation of hemidesmosomes in cells of a transformed murine mammary tumor cell line and mechanisms involved in adherence of these cells to laminin and kalinin J Cell Sci. 106:1083-1102.

Stepp M A, Gibson H E, Gala P H, Iglesia D D, Pajoohesh-Ganji A, Pal-Ghosh S, Brown M, Aquino C, Schwartz A M, Goldberger O, Hinkes M T and Bernfield M. (2002) Defects in keratinocyte activation during wound healing in the syndecan-1-deficient mouse. J. Cell Sci. 115, 4517-4531.

Sulka B, Lortat-Jacob H, Terreux R, Letourneur F, and Rousselle P. (2009) Tyrosine dephosphorylation of the syndecan-1 PDZ binding domain regulates syntenin-1 recruitment. J. Biol. Chem. February 19.

Timpl R, Tisi D, Talts J F, Andac Z, Sasaki T, and Hohenester E. (2000) Structure and function of laminin LG modules. Matrix Biol., 19:309-317.

Tisi D, Talts J F, Timpl R, a,d Hohenester E. Structure of the C-terminal laminin G-like domain pair of the laminin alpha2 chain harbouring binding sites for alpha-dystroglycan and heparin. Embo J. 2000, 19: 1432-1440.

Tunggal L, Ravaux J, Pesch M, Smola H, Krieg T, Gaill F, Sasaki T, Timpl R, Mauch, C and Aumailley M. (2002) Defective laminin 5 processing in cylindroma cells. Am. J. Pathol. 160:459-468.

Utani A, Nomizu M, Matsuura H, Kato K, Kobayashi T, Takeda U, Aota S, Nielsen P K and Shinkai H. (2001) A unique sequence of the laminin alpha 3 G domain binds to heparin and promotes cell adhesion through syndecan-2 and -4. J. Biol. Chem. 276:28779-28788.

Vivès R, Crublet E, Andieu J P, Gagnon J, Rousselle P, and Lortat-Jacob H. (2004) A novel strategy for defining critical amino acid residues involved in protein/glycosaminoglycan interactions. J. Biol. Chem., 279:54327-54333.

Woods, A, and Couchman JR. (2000) Integrin modulation by lateral association. J. Biol. Chem. 275, 24233-24236

The invention claimed is:

1. A method for treating tissue comprising the step of administering a synthetic peptide, the synthetic peptide consisting of at most 30 amino acids and comprising the sequence KKLRIKSKEK (SEQ ID NO: 1) or the sequence K$aa_2aa_3$R$aa_5aa_6aa_7aa_8aa_9aa_{10}$, wherein:
   $aa_2$, $aa_6$, $aa_8$, and/or $a_{10}$ is a positively charged residue at physiological pH, wherein:
   three of the four residues $aa_2$, $aa_6$, $aa_8$, and $aa_{10}$ or all four residues $aa_2$, $aa_6$, $aa_8$, and $aa_{10}$ are positively charged residues at physiological pH,
   at most one of the four residues aa is a neutrally charged residue at physiological pH,
   $aa_2$=K or A,
   $aa_3$ is a neutrally charged residue at physiological pH, wherein $aa_3$=A or L,
   $aa_5$ is a neutrally charged residue at physiological pH, wherein $aa_5$=A, L, I, K, S, T or H,
   $aa_6$=K, A, R or Q,
   $aa_7$ is a neutrally charged residue at physiological pH with the exception of alanine, wherein $aa_7$=S, L or Q,
   $aa_8$=K, A or Q,
   $aa_9$ is a negatively or neutrally charged residue at physiological pH, wherein $aa_9$=E or A, and $aa_{10}$=K, A, R or Q, and
wherein the sequence binds to the syndecan-1 receptor.

2. The method of claim 1, wherein the synthetic peptide comprises a sequence selected from the group consisting of:

| | |
|---|---|
| KALRIKSKEK | (SEQ ID NO: 2) |
| KKARIKSKEK | (SEQ ID NO: 3) |
| KKLRAKSKEK | (SEQ ID NO: 4) |
| KKLRIASKEK | (SEQ ID NO: 5) |
| KKLRIKSAEK | (SEQ ID NO: 6) |
| KKLRIKSKAK | (SEQ ID NO: 7) |
| KKLRIKSKEA | (SEQ ID NO: 8) |
| KKLRLRSKER | (SEQ ID NO: 9) |
| KKLRHKSKEK | (SEQ ID NO: 10) |
| KKLRTKSKEK | (SEQ ID NO: 11) |
| KKLRKKSKEK | (SEQ ID NO: 12) |
| KKLRSKSKEK | (SEQ ID NO: 13) |
| KKLRIKLKEK | (SEQ ID NO: 14) |
| KKLRIKQKEK | (SEQ ID NO: 15) |
| KKLRIQSKEK | (SEQ ID NO: 16) |
| KKLRIKSQEK, and | (SEQ ID NO: 17) |
| KKLRIKSKEQ | (SEQ ID NO: 18). |

3. The method of claim 1 wherein the synthetic peptide consists of the sequence KKLRIKSKEK (SEQ ID NO: 1).

4. A method for promoting the healing of skin comprising the step of administering a synthetic peptide, the synthetic peptide consisting of at most 30 amino acids and comprising the sequence KKLRIKSKEK (SEQ ID NO: 1) or the sequence K$aa_2aa_3$R$aa_5aa_6aa_7aa_8aa_9aa_{10}$ wherein:
   $aa_2$, $aa_6$, $aa_8$, and/or $a_{10}$ is a positively charged residue at physiological pH, wherein:
   three of the four residues $aa_2$, $aa_6$, $aa_8$, and $aa_{10}$ or all four residues $aa_2$, $aa_6$, $aa_8$, and $aa_{10}$ are positively charged residues at physiological pH,
   at most one of the four residues $aa_2$, $aa_6$, $aa_8$, and $aa_{10}$ is a neutrally charged residue at physiological pH,
   $aa_2$=K or A,
   $aa_3$ is a neutrally charged residue at physiological pH, wherein $aa_3$=A or L,
   $aa_5$ is a neutrally charged residue at physiological pH, wherein $aa_5$=A, L, I, K, S, T or H,
   $aa_6$=K, A, R or Q,
   $aa_7$ is a neutrally charged residue at physiological pH with the exception of alanine, wherein $aa_7$=S, L or Q,
   $aa_8$=K, A or Q,
   $aa_9$ is a negatively or neutrally charged residue at physiological pH, wherein $aa_9$=E or A, and $aa_{10}$=K, A, R or Q, and
wherein the sequence binds to the syndecan-1 receptor.

5. The method of claim 4 wherein the synthetic peptide consists of the sequence KKLRIKSKEK (SEQ ID NO: 1).

6. A method for promoting tissue regeneration comprising the step of administering a synthetic peptide, the synthetic peptide consisting of at most 30 amino acids and comprising the sequence KKLRIKSKEK (SEQ ID NO: 1) or the sequence K$aa_2aa_3$R$aa_5aa_6aa_7aa_8aa_9aa_{10}$, wherein:
   $aa_2$, $aa_6$, $aa_8$, and/or $a_{10}$ is a positively charged residue at physiological pH, wherein:
   three of the four residues $aa_2$, $aa_6$, $aa_8$, and $aa_{10}$ or all four residues $aa_2$, $aa_6$, $aa_8$, and $aa_{10}$ are positively charged residues at physiological pH,
   at most one of the four residues $aa_2$, $aa_6$, $aa_8$, and $aa_{10}$ is a neutrally charged residue at physiological pH,
   $aa_2$=K or A,
   $aa_3$ is a neutrally charged residue at physiological pH, wherein $aa_3$=A or L,
   $aa_5$ is a neutrally charged residue at physiological pH, wherein $aa_5$=A, L, I, K, S, T or H,
   $aa_6$=K, A, R or Q,
   $aa_7$ is a neutrally charged residue at physiological pH with the exception of alanine, wherein $aa_7$=S, L or Q,
   $aa_8$=K, A or Q,
   $aa_9$ is a negatively or neutrally charged residue at physiological pH wherein $aa_9$=E or A and $aa_{10}$=K, A, R or Q, and
wherein the sequence binds to the syndecan-1 receptor.

7. The method of claim 6 wherein the synthetic peptide consists of the sequence KKLRIKSKEK (SEQ ID NO: 1).

8. A composition comprising a synthetic peptide, wherein the synthetic peptide consists of at most 30 amino acids and comprises the sequence K$aa_2aa_3$R$aa_5aa_6aa_7aa_8aa_9aa_{10}$ wherein:
   $aa_2$, $aa_6$, $aa_8$, and/or $a_{10}$ is a positively charged residue at physiological pH, wherein:
   three of the four residues $aa_2$, $aa_6$, $aa_8$, and $aa_{10}$ or all four residues $aa_2$, $aa_6$, $aa_8$, and $aa_{10}$ are positively charged residues at physiological pH,
   at most one of the four residues $aa_2$, $aa_6$, $aa_8$, and $aa_{10}$, is a neutrally charged residue at physiological pH,
   $aa_2$=K or A,
   $aa_3$ is a neutrally charged residue at physiological pH, wherein $aa_3$=A or L,
   $aa_5$ is a neutrally charged residue at physiological pH, wherein $aa_5$=A, L, I, K, S, T or H,
   $aa_6$=K, A, R or Q, aa$_7$ is a neutrally charged residue at physiological pH with the exception of alanine,
wherein aa$_7$=S, L or Q,
aa$_8$=K, A or Q,
aa$_9$ is a negatively or neutrally charged residue at physiological pH, wherein aa$_9$=E or A, and
aa$_{10}$=K, A, R or Q,
wherein the sequence binds to the syndecan-1 receptor, and wherein when the synthetic peptide comprises the sequence KKLRIKSKEK (SEQ ID NO: 1), the synthetic peptide is 11 amino acids or less.

9. The composition of claim 8, in the form of a cream, a hydrogel, a solution, an injectable formulation or a spray.

10. The composition of claim 8 comprising autologous keratinocytes or mesenchymal cells.

11. The composition of claim 8 wherein the synthetic peptide is 11 amino acids or less and comprises or consists of the sequence KKLRIKSKEK (SEQ ID NO: 1).

12. The composition of claim 8, wherein the Kaa$_2$aa$_3$Raa$_5$aa$_6$aa$_7$aa$_8$aa$_9$aa$_{10}$ sequence consists of a sequence selected from the group consisting of:

| | |
|---|---|
| KKLRIKSKEK | (SEQ ID NO: 1) |
| KALRIKSKEK | (SEQ ID NO: 2) |
| KKARIKSKEK | (SEQ ID NO: 3) |
| KKLRAKSKEK | (SEQ ID NO: 4) |
| KKLRIASKEK | (SEQ ID NO: 5) |
| KKLRIKSAEK | (SEQ ID NO: 6) |
| KKLRIKSKAK | (SEQ ID NO: 7) |
| KKLRIKSKEA | (SEQ ID NO: 8) |
| KKLRLRSKER | (SEQ ID NO: 9) |
| KKLRHKSKEK | (SEQ ID NO: 10) |
| KKLRTKSKEK | (SEQ ID NO: 11) |
| KKLRKKSKEK | (SEQ ID NO: 12) |
| KKLRSKSKEK | (SEQ ID NO: 13) |
| KKLRIKLKEK | (SEQ ID NO: 14) |
| KKLRIKQKEK | (SEQ ID NO: 15) |
| KKLRIQSKEK | (SEQ ID NO: 16) |
| KKLRIKSQEK | (SEQ ID NO: 17) |
| KKLRIKSKEQ. | (SEQ ID NO: 18) |

13. A medical device comprising a synthetic peptide, wherein the medical device is in the form of a support onto which is grafted or deposited, or within which is incorporated, the synthetic peptide, and wherein the synthetic peptide consists of at most 30 amino acids and comprises the sequence Kaa$_2$aa$_3$Raa$_5$aa$_6$aa$_7$aa$_8$aa$_9$aa$_{10}$ wherein:
aa$_2$, aa$_6$, aa$_8$, and/or a$_{10}$ is a positively charged residue at physiological pH, wherein:
three of the four residues aa$_2$, aa$_6$, aa$_8$, and aa$_{10}$ or all four residues aa$_2$, aa$_6$, aa$_8$, and aa$_{10}$ are positively charged residues at physiological pH,
at most one of the four residues aa$_2$, aa$_6$, aa$_8$, and aa$_{10}$, is a neutrally charged residue at physiological pH,
aa$_2$=K or A,
aa$_3$ is a neutrally charged residue at physiological pH, wherein aa$_3$=A or L,
aa$_5$ is a neutrally charged residue at physiological pH, wherein aa$_5$=A, L, I, K, S, T or H,
aa$_6$=K, A, R or Q,
aa$_7$ is a neutrally charged residue at physiological pH with the exception of alanine, wherein aa$_7$=S, L or Q,
aa$_8$=K, A or Q,
aa$_9$ is a negatively or neutrally charged residue at physiological pH, wherein aa$_9$=E or A,
aa$_{10}$=K, A, R or Q, and
wherein the sequence binds to the syndecan-1 receptor.

14. The medical device of claim 13, wherein the support is in the form of a film or a matrix comprising:
a biological material selected from the group consisting of collagen, gelatine, polysaccharide, hyaluronic acid, cellulose, carboxymethylcellulose, pectin, chitosan, human or animal acellular dermis, or
a synthetic material selected from the group consisting of silicone, polyurethane, PLLA, or
a textile dressing material selected from the group consisting of cotton, polyester and polyamide.

15. The medical device of claim 13 wherein the synthetic peptide comprises or consists of the sequence KKLRIKSKEK (SEQ ID NO: 1).

16. The medical device of claim 13, wherein the Kaa$_2$aa$_3$Raa$_5$aa$_6$aa$_7$aa$_8$aa$_9$aa$_{10}$ sequence is selected from the group consisting of:

| | |
|---|---|
| KKLRIKSKEK | (SEQ ID NO: 1) |
| KALRIKSKEK | (SEQ ID NO: 2) |
| KKARIKSKEK | (SEQ ID NO: 3) |
| KKLRAKSKEK | (SEQ ID NO: 4) |
| KKLRIASKEK | (SEQ ID NO: 5) |
| KKLRIKSAEK | (SEQ ID NO: 6) |
| KKLRIKSKAK | (SEQ ID NO: 7) |
| KKLRIKSKEA | (SEQ ID NO: 8) |
| KKLRLRSKER | (SEQ ID NO: 9) |
| KKLRHKSKEK | (SEQ ID NO: 10) |
| KKLRTKSKEK | (SEQ ID NO: 11) |
| KKLRKKSKEK | (SEQ ID NO: 12) |
| KKLRSKSKEK | (SEQ ID NO: 13) |
| KKLRIKLKEK | (SEQ ID NO: 14) |
| KKLRIKQKEK | (SEQ ID NO: 15) |
| KKLRIQSKEK | (SEQ ID NO: 16) |
| KKLRIKSQEK | (SEQ ID NO: 17) |
| KKLRIKSKEQ. | (SEQ ID NO: 18) |

17. A culture medium comprising a synthetic peptide wherein the synthetic peptide consists of at most 30 amino acids and comprises the sequence Kaa$_2$aa$_3$Raa$_5$aa$_6$aa$_7$aa$_8$aa$_9$aa$_{10}$ wherein:
aa$_2$, aa$_6$, aa$_8$, and/or a$_{10}$ is a positively charged residue at physiological pH, wherein:
three of the four residues aa$_2$, aa$_6$, aa$_8$, and aa$_{10}$ or all four residues aa$_2$, aa$_6$, aa$_8$, and aa$_{10}$ are positively charged residues at physiological pH, at most one of the four residues $aa_2$, $aa_6$, $aa_8$, and $aa_{10}$, is a neutrally charged residue at physiological pH, $aa_2$=K or A, $aa_3$ is a neutrally charged residue at physiological pH, wherein $aa_3$=A or L, $aa_5$ is a neutrally charged residue at physiological pH, wherein $aa_5$=A, L, I, K, S, T or H, $aa_6$=K, A, R or Q, $aa_7$ is a neutrally charged residue at physiological pH with the exception of alanine, wherein $aa_7$=S, L or Q, $aa_8$=K, A or Q, $aa_9$ is a negatively or neutrally charged residue at physiological pH, wherein $aa_9$=E or A, $aa_{10}$=K, A, R or Q, and wherein the sequence binds to the syndecan-1 receptor.

18. The culture medium of claim 17 wherein the synthetic peptide comprises or consists of the sequence KKLRIKSKEK (SEQ ID NO: 1).

19. The culture medium of claim 17, wherein the $Kaa_2aa_3Raa_5aa_6aa_7aa_8aa_9aa_{10}$ sequence is selected from the group consisting of:

```
KKLRIKSKEK,     (SEQ ID NO: 1)
KALRIKSKEK,     (SEQ ID NO: 2)
KKARIKSKEK,     (SEQ ID NO: 3)
KKLRAKSKEK,     (SEQ ID NO: 4)
KKLRIASKEK,     (SEQ ID NO: 5)
KKLRIKSAEK,     (SEQ ID NO: 6)
KKLRIKSKAK,     (SEQ ID NO: 7)
KKLRIKSKEA,     (SEQ ID NO: 8)
KKLRLRSKER,     (SEQ ID NO: 9)
KKLRHKSKEK,     (SEQ ID NO: 10)
KKLRTKSKEK,     (SEQ ID NO: 11)
KKLRKKSKEK,     (SEQ ID NO: 12)
KKLRSKSKEK,     (SEQ ID NO: 13)
KKLRIKLKEK,     (SEQ ID NO: 14)
KKLRIKQKEK,     (SEQ ID NO: 15)
KKLRIQSKEK,     (SEQ ID NO: 16)
KKLRIKSQEK,     (SEQ ID NO: 17)
and
KKLRIKSKEQ      (SEQ ID NO: 18).
```

20. A support for the culture of epithelial cells comprising: a support onto which is grafted or adsorbed a synthetic peptide, wherein the synthetic peptide consists of at most 30 amino acids and comprises the sequence $Kaa_2aa_3Raa_5aa_6aa_7aa_8aa_9aa_{10}$ wherein:

$aa_2$, $aa_6$, $aa_8$, and/or $a_{10}$ is a positively charged residue at physiological pH, wherein:

three of the four residues $aa_2$, $aa_6$, $aa_8$, and $aa_{10}$ or all four residues $aa_2$, $aa_6$, $aa_8$, and $aa_{10}$ are positively charged residues at physiological pH, at most one of the four residues $aa_2$, $aa_6$, $aa_8$, and $aa_{10}$, is a neutrally charged residue at physiological pH, $aa_2$=K or A, $aa_3$ is a neutrally charged residue at physiological pH, wherein $aa_3$=A or L, $aa_5$ is a neutrally charged residue at physiological pH, wherein $aa_5$=A, L, I, K, S, T or H, $aa_6$=K, A, R or Q, $aa_7$ is a neutrally charged residue at physiological pH with the exception of alanine, wherein $aa_7$=S, L or Q, $aa_8$=K, A or Q, $aa_9$ is a negatively or neutrally charged residue at physiological pH, wherein $aa_9$=E or A, $aa_{10}$=K, A, R or Q, and wherein the sequence binds to the syndecan-1 receptor, the support being in the form of a polystyrene culture dish, a film or a porous matrix made of biopolymer, a textile membrane or gel collagen.

21. The support of claim 20 wherein the synthetic peptide comprises or consists of the sequence KKLRIKSKEK (SEQ ID NO: 1).

22. The support of claim 20, wherein the $Kaa_2aa_3Raa_5aa_6aa_7aa_8aa_9aa_{10}$ sequence is selected from the group consisting of:

```
KKLRIKSKEK,     (SEQ ID NO: 1)
KALRIKSKEK,     (SEQ ID NO: 2)
KKARIKSKEK,     (SEQ ID NO: 3)
KKLRAKSKEK,     (SEQ ID NO: 4)
KKLRIASKEK,     (SEQ ID NO: 5)
KKLRIKSAEK,     (SEQ ID NO: 6)
KKLRIKSKAK,     (SEQ ID NO: 7)
KKLRIKSKEA,     (SEQ ID NO: 8)
KKLRLRSKER,     (SEQ ID NO: 9)
KKLRHKSKEK,     (SEQ ID NO: 10)
KKLRTKSKEK,     (SEQ ID NO: 11)
KKLRKKSKEK,     (SEQ ID NO: 12)
KKLRSKSKEK,     (SEQ ID NO: 13)
KKLRIKLKEK,     (SEQ ID NO: 14)
KKLRIKQKEK,     (SEQ ID NO: 15)
KKLRIQSKEK,     (SEQ ID NO: 16)
KKLRIKSQEK,     (SEQ ID NO: 17)
and
KKLRIKSKEQ      (SEQ ID NO: 18).
```

23. A method for in vitro culturing of epithelial or mesenchymal cells comprising the step of providing a culture medium, the culture medium comprising a synthetic peptide, the synthetic peptide consisting of at most 30 amino acids and comprising the sequence KKLRIKSKEK (SEQ ID NO: 1) or the sequence $Kaa_2aa_3Raa_5aa_6aa_7aa_8aa_9aa_{10}$, wherein:

$aa_2$, $aa_6$, $aa_8$, and/or $a_{10}$ is a positively charged residue at physiological pH, wherein:

three of the four residues $aa_2$, $aa_6$, $aa_8$, and $aa_{10}$ or all four residues $aa_2$, $aa_6$, $aa_8$, and $aa_{10}$ are positively charged residues at physiological pH, at most one of the four residues $aa_2$, $aa_6$, $aa_8$, and $aa_{10}$ is a neutrally charged residue at physiological pH, $aa_2$=K or A, $aa_3$ is a neutrally charged residue at physiological pH, wherein $aa_3$=A or L, aa$_5$ is a neutrally charged residue at physiological pH, wherein aa$_5$=A, L, I, K, S, T or H, aa$_6$=K, A, R or Q, aa$_7$ is a neutrally charged residue at physiological pH with the exception of alanine, wherein aa$_7$=S, L or Q, aa$_8$=K, A or Q, aa$_9$ is a negatively or neutrally charged residue at physiological pH wherein aa$_9$=E or A and aa$_{10}$=K, A, R or Q, and wherein the sequence binds to the syndecan-1 receptor.

24. The method of claim 23 wherein the synthetic peptide comprises or consists of the sequence KKLRIKSKEK (SEQ ID NO: 1).

25. The method of claim 23, wherein the Kaa$_2$aa$_3$Raa$_5$aa$_6$aa$_7$aa$_8$aa$_9$aa$_{10}$ sequence is selected from the group consisting of:

| | |
|---|---|
| KKLRIKSKEK, | (SEQ ID NO: 1) |
| KALRIKSKEK, | (SEQ ID NO: 2) |
| KKARIKSKEK, | (SEQ ID NO: 3) |
| KKLRAKSKEK, | (SEQ ID NO: 4) |
| KKLRIASKEK, | (SEQ ID NO: 5) |
| KKLRIKSAEK, | (SEQ ID NO: 6) |
| KKLRIKSKAK, | (SEQ ID NO: 7) |
| KKLRIKSKEA, | (SEQ ID NO: 8) |
| KKLRLRSKER, | (SEQ ID NO: 9) |
| KKLRHKSKEK, | (SEQ ID NO: 10) |
| KKLRTKSKEK, | (SEQ ID NO: 11) |
| KKLRKKSKEK, | (SEQ ID NO: 12) |
| KKLRSKSKEK, | (SEQ ID NO: 13) |
| KKLRIKLKEK, | (SEQ ID NO: 14) |
| KKLRIKQKEK, | (SEQ ID NO: 15) |
| KKLRIQSKEK, | (SEQ ID NO: 16) |
| KKLRIKSQEK, and | (SEQ ID NO: 17) |
| KKLRIKSKEQ | (SEQ ID NO: 18). |

* * * * *

UNITED STATES PATENT AND TRADEMARK OFFICE
CERTIFICATE OF CORRECTION

PATENT NO. : 9,260,507 B2  
APPLICATION NO. : 13/255299  
DATED : February 16, 2016  
INVENTOR(S) : Patricia Rousselle Page 1 of 1

It is certified that error appears in the above-identified patent and that said Letters Patent is hereby corrected as shown below:

Claim 1, column 41, line 7, delete "$a_{10}$" and replace with "$aa_{10}$".

Claim 4, column 42, line 1, delete "$a_{10}$" and replace with "$aa_{10}$".

Signed and Sealed this  
Fourteenth Day of June, 2016

Michelle K. Lee  
*Director of the United States Patent and Trademark Office*